US005663168A

United States Patent [19]
Rösel et al.

[11] Patent Number: 5,663,168
[45] Date of Patent: Sep. 2, 1997

[54] USE OF COMPOSITIONS FOR COMBATING TUMOUR DISEASES

[75] Inventors: Johannes Rösel, Riehen; Urs Regenass, Ettingen, both of Switzerland; Marc Lang, Mulhouse, France; Guido Bold, Gipf-Oberfrick, Switzerland; Frédéric Cumin, Hagental-Le-Bas, France

[73] Assignee: CIBA-Geigy Corporation, Tarrytown, N.Y.

[21] Appl. No.: 242,915

[22] Filed: May 16, 1994

[30] Foreign Application Priority Data

May 17, 1993 [CH] Switzerland ................ 1492/93

[51] Int. Cl.$^6$ ................ A61K 31/54; A61K 31/535; A61K 38/00
[52] U.S. Cl. ................ 514/227.5; 514/227.8; 514/231.5; 514/235.5; 514/17; 514/18; 514/19
[58] Field of Search ................ 514/17, 18, 19, 514/227.5, 227.8, 231.5, 235.5

[56] References Cited

FOREIGN PATENT DOCUMENTS

| | | |
|---|---|---|
| 0337714 | 10/1989 | European Pat. Off. . |
| 0356223 | 2/1990 | European Pat. Off. . |
| 0356595 | 3/1990 | European Pat. Off. . |
| 0434365 | 6/1991 | European Pat. Off. . |
| 0532466 | 3/1993 | European Pat. Off. . |
| 0566237 | 10/1993 | European Pat. Off. . |
| 89/9558 | 8/1990 | South Africa . |
| 91/4136 | 2/1992 | South Africa . |
| 92/6938 | 2/1993 | South Africa . |
| 92/4914 | 3/1993 | South Africa . |
| 9208701 | 5/1992 | WIPO . |
| 9221373 | 12/1992 | WIPO . |
| 9301174 | 1/1993 | WIPO . |
| 9304055 | 3/1993 | WIPO . |
| 9405285 | 3/1994 | WIPO . |

OTHER PUBLICATIONS

Shoeman et al, "Potential Role of the Viral Protease in Human Immuno-deficiency Virus Type 1 Associated Pathogens", Medical Hypotheses 37, 137–150, 1992.
Chem. Abst. 115: 78928 (1991).
Carter et al, Chemotherapy of Cancer, 2nd ed., John Wiley & Sons, N.Y., N.Y. pp. 67–68 (1981).

*Primary Examiner*—Jerome D. Goldberg
*Attorney, Agent, or Firm*—Marla J. Mathias; Irving M. Fishman

[57] ABSTRACT

The present invention relates to the use of inhibitors of HIV aspartate proteases, such as HIV-1- or HIV-2-protease, and their salts and to prodrugs for inhibiting the growth of tumors, especially those tumors which do not respond to the inhibition of HIV aspartate proteases themselves, and in the preparation of pharmaceutical compositions intended for use in the prophylaxis and especially the treatment of tumor diseases, and to methods and pharmaceutical compositions for the treatment of tumors with those compounds.

11 Claims, No Drawings

USE OF COMPOSITIONS FOR COMBATING TUMOUR DISEASES

The present invention relates to the use of compounds described as inhibitors of HIV aspartate proteases, such as HIV-1- or HIV-2-protease, and salts thereof, especially the pharmaceutically acceptable salts thereof, in the treatment of tumour diseases and in the preparation of pharmaceutical compositions intended for use in the prophylaxis and, especially, the treatment of tumour diseases, and to methods of treating tumours with those compounds and to corresponding pharmaceutical compositions.

The above-mentioned inhibitors of HIV aspartate proteases, such as HIV-1- or HIV-2-protease from HIV-1 or HIV-2, which are considered to be and are described as organisms causing AIDS, the salts thereof and the preparation thereof, are especially those described in the European Patent Application having the application number 92 810 678.0 and the publication number EP 0 532 466, issued in the name of the Applicants of the present invention and published on 17th Mar., 1993, in the European Patent Application having the application number 89 303 539.4 and the publication number EP 0 337 714, issued in the name of Merck & Co., Inc., New Jersey, and published on Oct. 18, 1989, in the European Patent Application having the application number 89 308 555.5 and the publication number EP 0 356 223, issued in the name of Merck & Co., Inc., New Jersey, and published on Feb. 28, 1990, in the European Patent Application having the application number 90 313 848.5 and the publication number EP 0 434 365, issued in the name of Merck & Co., Inc., New Jersey, and published on Jun. 26, 1991, in the European Patent Application having the application number 91 108 828.4 and the publication number EP 0 459 465, issued in the name of the Applicants of the present invention and published on 4th Dec., 1991, or in the European Patent Application having the application number 89 810 923.6 and the publication number EP 0 374 098, issued in the name of the Applicants of the present invention and published on 20th Jun., 1990. The use according to the invention is not suggested in any of those applications. English-language equivalents of the two last-mentioned applications are the corresponding South African Patents ZA 91/4136 (granted on 26th Feb., 1992) and ZA 89/9558 (granted on 29th Aug., 1990). The said patent applications are herewith incorporated by reference; especially the individual compounds mentioned therein are to be regarded as being included by reference in the present description for use according to the invention. Also possible are compounds esterified at hydroxy groups, for example esterified by lower alkanoyl, such as acetyl, or especially by lower alkoxy-lower alkoxy-lower alkanoyl or lower alkoxy-lower alkoxy-lower alkoxy-lower alkanoyl (which can be prepared by reaction of the free compounds with activated or in situ activated lower alkoxy-lower alkoxy-lower alkanoic acids or lower alkoxy-lower alkoxy-lower alkoxy-lower alkanoic acids, such as the acid chlorides, which can be prepared, for example, in methylene chloride with 1-chloro-N,N,2-trimethyl-1-propenamine at approximately 0° C., and subsequent reaction of the acid chlorides (for example after isolation by concentration by evaporation) in dioxane with the respective inhibitor of HIV aspartate protease with a free hydroxy group in the presence of pyridine).

The compounds are preferably those of formula

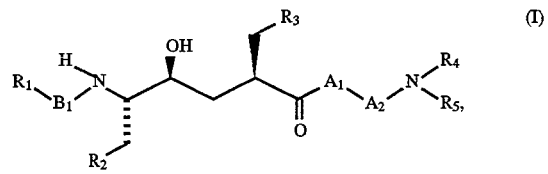

(I)

wherein
$R_1$ is hydrogen; lower alkoxycarbonyl; heterocyclylcarbonyl; benzyloxycarbonyl which is unsubstituted or substituted by up to three radicals selected independently of one another from fluorine, halo-lower alkyl, lower alkanoyl, sulfo, lower alkylsulfonyl and cyano; heterocyclyloxycarbonyl wherein heterocyclyl is bonded via a carbon atom; one of the mentioned carbonyl radicals wherein the bonding carbonyl group has been replaced by a thiocarbonyl group; heterocyclylsulfonyl; lower alkylsulfonyl; or N-(heterocyclyl-lower alkyl)-N-lower alkyl-aminocarbonyl;

$B_1$ is a bond or a bivalent residue of an α-amino acid bonded N-terminally to $R_1$ and C-terminally to the amino group at the carbon atom carrying $R_2$—$CH_2$—, $R_2$ and $R_3$ are each independently of the other phenyl or cyclohexyl, those radicals being unsubstituted or being substituted by from one to three radicals selected independently of one another from hydroxy, lower alkoxy, halogen, halo-lower alkyl, sulfo, lower alkylsulfonyl, cyano and nitro, $A_1$ is a bond between —C=O and $A_2$ or is a bivalent residue of an α-amino acid bonded N-terminally to the group —C=O and C-terminally to $A_2$, $A_2$ is a bivalent residue of an α-amino acid bonded N-terminally to $A_1$ and C-terminally to the group $NR_4R_5$, or $A_1$ and $A_2$ together form a bivalent residue of a dipeptide the central amide bond of which has been reduced and which is bonded N-terminally to the group —C=O and C-terminally to the group $NR_4R_5$, and $R_4$ and $R_5$ together with the bonding nitrogen atom form unsubstituted or substituted thiomorpholino or morpholino, or salts of those compounds where salt-forming groups are present, or hydroxy-protected derivatives of those compounds or salts thereof, which, together with their method of preparation, are described in the European Patent Application having the application number 92 810 678.0 and the publication number EP 0 532 466, issued in the name of the Applicants of this invention and published on 17th Mar., 1993.

The compounds used according to the invention and their salts are known as active ingredients for combating diseases caused by HIV, such as AIDS. The mode of action lies in the inhibition of an HIV aspartate protease which the retrovirus in question itself encodes in its genome and which is necessary for the maturation of complete new virions.

Since tumour diseases are one of the main causes of death in the world today, the provision of ways and means of treating tumours is a constant goal. In particular, owing to the large number and the variety of possible tumour diseases, there is a constant need for new pharmaceutical compositions which by virtue of their active ingredients are suitable for the treatment either of as many tumours as possible or of very specific tumours.

According to the invention it has now surprisingly been found that the inhibitors of HIV aspartate proteases mentioned hereinabove and hereinbelow have a marked activity in the prevention and treatment of tumour diseases, including the formation of metastases, as can be seen, for example, from animal experiments illustrated by way of example in the Examples section. In those animal experiments, observations are made of warm-blooded animals, such as rats, guinea pigs and especially mice, suffering from a tumour disease or caused to suffer from a tumour disease as a result of the administration of tumour cells (for example by transplantation of fragments of tumour or by injection of tumour cell lines), which before, simultaneously with or after the onset of a tumour disease are treated with one of the inhibitors of HIV aspartate proteases mentioned hereinabove and hereinbelow, especially of formula I, or with a salt thereof. The said inhibitors of HIV aspartate proteases inhibit the growth of tumours. They are valuable active ingredients against tumour diseases.

The good activity of the inhibitors of HIV aspartate proteases mentioned hereinabove and hereinbelow against tumour diseases, especially those having invasive tumour growth and the formation of metastases, especially tumours of the pancreas, lungs, intestine, ovaries or breast, is remarkable.

The inhibitors of HIV aspartate proteases mentioned hereinabove and hereinbelow, especially of formula I, can be used especially for the prophylaxis and treatment of tumour diseases, for example also the formation of tumour metastases, that form the basis of cytokine- or hormone-dependent types of tumour, such as tumours of the pancreas, lungs, intestine, ovaries or breast.

The above-mentioned inhibitors of HIV aspartate proteases, especially of formula I, are used especially in the case of oestrogen-dependent tumour diseases, for example tumours of the pancreas, intestine or breast, that exhibit oestrogen-dependent growth, and metastases thereof.

The above-mentioned inhibitors of HIV aspartate proteases, especially of formula I, are used more especially in the case of oestrogen-dependent tumours of the breast, and metastases thereof, for example in axillary lymph nodes.

The mentioned tumour diseases to be treated are especially diseases relating to tumours which are not responsive to the inhibition of HIV aspartate proteases (for example HIV-1- and/or HIV-2-protease) themselves.

Examples of the inhibition of aspartate proteases and corresponding test methods can be found in Jupp et al., Biochem. J. 265, 871–878 (1990), while the inhibition of HIV-1-protease can take place, for example, in accordance with the method described in EP 0 532 466 (see above).

The inhibitors of HIV aspartate proteases, especially of formula I, can be used as such or in the form of pharmaceutical compositions, by administering them enterally or parenterally together with suitable excipients or carriers to warm-blooded animals, especially human beings. They are preferably applied to the mucosa, for example intranasally, rectally or vaginally or to the conjunctiva of the eyes, or orally or by other routes, for example subcutaneously, intravenously, intramuscularly or intraperitoneally, or by application to normal skin.

The dose of the active ingredient depends inter alia upon the species of warm-blooded animal, the defensive condition of the organism, the mode of administration and the nature and location of the tumour disease.

According to the invention the inhibitors of aspartate proteases, especially of formula I, are used in the preparation of pharmaceutical compositions that comprise (especially in the treatment of tumour diseases in warm-blooded animals, especially human beings, requiring such treatment) a pharmacologically effective amount of the active ingredient together with significant amounts of (at least one) pharmaceutically acceptable carrier(s) that are suitable for enteral, for example oral, or parenteral administration and are inorganic or organic, solid or liquid.

The pharmaceutical compositions that can be prepared according to the invention are compositions for enteral, such as nasal, buccal, rectal or oral, or parenteral, such as intramuscular or intravenous, administration to warm-blooded animals (human beings and animals) that comprise an effective dose of the pharmacological active ingredient alone or together with a significant amount of a pharmaceutically acceptable carrier. The dose of the active ingredient depends upon the species of warm-blooded animal, body weight, age and individual condition, individual pharmacokinetic data, the disease to be treated and the mode of administration.

The invention relates also to pharmaceutical compositions for use in a method for the therapeutic treatment of the human or animal body, a process for the preparation thereof (especially as agents in the treatment of tumours) and a method of treating tumour diseases, especially those mentioned above.

Within the scope of the method of treating tumours in warm-blooded animals suffering from a tumour disease, there is administered, especially to warm-blooded animals requiring such treatment, an inhibitor of HIV aspartate proteases, especially a compound of formula I, or a pharmaceutically acceptable salt thereof, in an amount effective against the tumour disease. In the method of treating tumour diseases in warm-blooded animals there is administered, especially to warm-blooded animals requiring such treatment, an inhibitor of HIV aspartate proteases, or a pharmaceutically acceptable salt thereof where salt-forming groups are present, in an amount effective against tumour diseases.

The doses to be administered to warm-blooded animals, for example human beings of approximately 70 kg body weight, vary in accordance with species, age, individual condition, mode of administration and the syndrome in question, and are especially from approximately 3 mg to approximately 10 g, preferably from approximately 40 mg to approximately 4 g, for example approximately from 150 mg to 1.5 g per person per day, divided preferably into 1 to 3 single doses which may, for example, be of the same size. Usually, children receive half of the adult dose. If necessary, the treatment may be continued for as long as is necessary to treat the tumour and/or to prevent the formation of metastases.

The inhibitors of HIV aspartate proteases, especially of formula I, can be used alone or in combination with other pharmacologically effective substances. They could be used, for example, in combination with (a) inhibitors of enzymes of polyamine biosynthesis, for example ornithine decarboxylase inhibitors or S-adenosylmethionine decarboxylase inhibitors, (b) inhibitors of protein kinase C, (c) inhibitors of tyrosine protein kinase, (d) cytokines, (e) negative growth regulators, (f) aromatase inhibitors, (g) anti-oestrogens or (h) classic cytostatic active ingredients, such as adriamycin.

The pharmaceutical compositions comprise from approximately 1% to approximately 95%, preferably from approximately 20% to approximately 90%, active ingredient. Pharmaceutical compositions prepared according to the invention may be, for example, in unit dose form, such as in the form of ampoules, vials, suppositories, dragées, tablets or capsules. Other dosage forms are, for example, ointments, creams, pastes, foams, tinctures, lipsticks, drops, sprays, dispersions, etc..

According to the invention, the pharmaceutical compositions are prepared in a manner known per se, for example by means of conventional dissolving, lyophilising, mixing, granulating or confectioning processes.

Solutions of the active ingredient, and also suspensions or dispersions, and especially isotonic aqueous solutions, dispersions or suspensions, are preferably used, it being possible, for example in the case of lyophilised compositions that comprise the active ingredient alone or together with a carrier, for example mannitol, for such solutions, dispersions or suspensions to be made up prior to use. The pharmaceutical compositions may be sterilised and/or may comprise excipients, for example preservatives, stabilisers, wetting agents and/or emulsifiers, solubilisers, salts for regulating the osmotic pressure and/or buffers, and are prepared in a manner known per se, for example by means of conventional dissolving or lyophilising processes. The said solutions or suspensions may comprise viscosity-increasing substances, such as sodium carboxymethylcellulose, carboxymethylcellulose, dextran, polyvinylpyrrolidone or gelatin.

Suspensions in oil comprise as the oil component the vegetable, synthetic or semi-synthetic oils customary for injection purposes. There may be mentioned as such especially liquid fatty acid esters that contain as the acid component a long-chained fatty acid having from 8 to 22, especially from 12 to 22, carbon atoms, for example lauric acid, tridecylic acid, myristic acid, pentadecylic acid, palmitic acid, margaric acid, stearic acid, arachidic acid, behenic acid or corresponding unsaturated acids, for example oleic acid, elaidic acid, erucic acid, brassidic acid or linoleic acid, if desired with the addition of antioxidants, for example vitamin E, β-carotene or 3,5-di-tert-butyl-4-hydroxytoluene. The alcohol component of those fatty acid esters has a maximum of 6 carbon atoms and is a mono- or poly-hydric, for example a mono-, di- or tri-hydric, alcohol, for example methanol, ethanol, propanol, butanol or pentanol or the isomers thereof, but especially glycol and glycerol. The following examples of fatty acid esters are therefore to be mentioned: ethyl oleate, isopropyl myristate, isopropyl palmitate, "Labrafil M 2375" (polyoxyethylene glycerol trioleate, Gattefossé, Paris), "Miglyol 812" (triglyceride of saturated fatty acids with a chain length of $C_8$ to $C_{12}$, Hüls AG, Germany), but especially vegetable oils, such as cottonseed oil, almond oil, olive oil, castor oil, sesame oil, soybean oil and more especially groundnut oil.

The injection compositions are prepared in customary manner under sterile conditions; the same applies also to introducing the compositions into ampoules or vials and sealing the containers.

Pharmaceutical compositions for oral administration can be obtained by combining the active ingredient with solid carriers, if desired granulating a resulting mixture, and processing the mixture, if desired or necessary, after the addition of appropriate excipients, into tablets, dragée cores or capsules, or by preparing dispersions, preferably with phospholipids, which are introduced into vials. It is also possible for the active ingredients to be incorporated into plastics carriers that allow the active ingredients to diffuse or be released in measured amounts.

Suitable carriers are especially fillers, such as sugars, for example lactose, dextrose, sucrose, saccharose, glycerol, mannitol or sorbitol, cellulose preparations and/or calcium phosphates, for example tricalcium phosphate or calcium hydrogen phosphate, and also binders, such as magnesium aluminium silicate, starch pastes using, for example, corn, wheat, rice or potato starch, gelatin, tragacanth, methylcellulose, hydroxypropylmethylcellulose, sodium carboxymethylcellulose and/or polyvinylpyrrolidone, and/or, if desired, disintegrators, such as the above-mentioned starches, also carboxymethyl starch, cross-linked polyvinylpyrrolidone, agar, alginic acid or a salt thereof, such as sodium alginate. Excipients are especially flow conditioners and lubricants, for example silicic acid, talc, stearic acid or salts thereof, such as magnesium or calcium stearate, and/or polyethylene glycol. Dragée cores are provided with suitable, optionally enteric, coatings, there being used, inter alia, concentrated sugar solutions which may comprise gum arabic, talc, polyvinylpyrrolidone, polyethylene glycol and/or titanium dioxide, or coating solutions in suitable organic solvents, or, for the preparation of enteric coatings, solutions of suitable cellulose preparations, such as ethylcellulose phthalate or hydroxypropylmethylcellulose phthalate. Capsules are dry-filled capsules made of gelatin and also soft, sealed capsules made of gelatin and a plasticiser, such as glycerol or sorbitol. The dry-filled capsules may comprise the active ingredient in the form of granules, for example with fillers, such as lactose, binders, such as starches, and/or glidants, such as talc or magnesium stearate, and if desired with stabilisers. In soft capsules the active ingredient is preferably dissolved or suspended in suitable oily excipients, such as fatty oils, paraffin oil or liquid polyethylene glycols, it likewise being possible for stabilisers and/or antibacterial agents to be added. To the tablets or dragée coatings or to the capsule casings there may be added dyes or pigments, for example for identification purposes or to indicate different doses of active ingredient, or flavourings or sweeteners.

Especially preferred as pharmaceutical compositions are phospholipid-stabilised dispersions of the active ingredient, preferably for oral administration, comprising
a) a phospholipid or several phospholipids of the formula

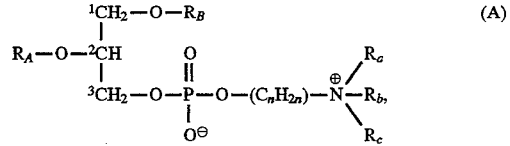

wherein $R_A$ is $C_{10-20}$acyl, $R_B$ is hydrogen or $C_{10-20}$acyl, $R_a$, $R_b$ and $R_c$ are hydrogen or $C_{1-4}$alkyl and n is an integer from two to four, if desired
b) a further phospholipid or several further phospholipids
c) the active ingredient and
d) a pharmaceutically acceptable carrier liquid and, if desired, further excipients and/or preservatives.

The process for the preparation of those dispersions is as follows: a solution or suspension of components a) and c) or a), b) and c), but preferably of a) and b) in a ratio by weight of from 20:1 to 1:5, especially from 5:1 to 1:1, is converted into a dispersion by dilution with water and the organic solvent is then removed, for example by centrifugation, gel filtration, ultrafiltration or especially by dialysis, for example tangential dialysis, preferably against water, and then, preferably after the addition of excipients or preservatives and if necessary with the establishment of an acceptable pH value by the addition of pharmaceutically acceptable buffers, such as phosphate salts or organic acids (pure or dissolved in water), such as acetic acid or citric acid, preferably from pH 3 to 6, for example pH 4–5, the dispersion obtained is concentrated (unless it already has the correct active ingredient concentration), preferably to an active ingredient concentration of from 2 to 30 mg/ml, especially from 10 to 20 mg/ml, concentration preferably being effected in accordance with the methods last mentioned for the removal of an organic solvent, especially by ultrafiltration, for example using an apparatus for carrying out tangential dialysis and ultrafiltration.

The phospholipid-stabilised dispersion that can be prepared in accordance with that process is stable for at least several hours at room temperature, is reproducible as regards the proportions of the components and is toxicologically acceptable and is therefore especially suitable for oral administration to human beings.

The size of the particles obtained in the dispersion is variable and is preferably from approximately $1.0 \times 10^{-8}$ to approximately $1.0 \times 10^{-5}$ m, especially from approximately $10^{-7}$ to approximately $2 \times 10^{-6}$ m.

The nomenclature for the phospholipids of formula A and the numbering of the carbon atoms are in accordance with the recommendations of the IUPAC-IUB Commission on Biochemical Nomenclature (CBN) (sn-nomenclature, stereospecific numbering) given in the Eur. J. of Biochem. 79, 11–21 (1977) "Nomenclature of Lipids".

In a phospholipid of formula A, $R_A$ and $R_B$ having the definitions $C_{10-20}$acyl are preferably straight-chained $C_{10-20}$alkanoyl having an even number of carbon atoms and straight-chained $C_{10-20}$alkenoyl having a double bond and an even number of carbon atoms.

Straight-chained $C_{10-20}$alkanoyl $R_A$ and $R_B$ having an even number of carbon atoms are, for example, n-dodecanoyl, n-tetradecanoyl, n-hexadecanoyl or n-octadecanoyl.

Straight-chained $C_{10-20}$alkenoyl $R_A$ and $R_B$ having a double bond and an even number of carbon atoms are, for example, 6-cis-, 6-trans-, 9-cis- or 9-trans-dodecenoyl, -tetradecenoyl, -hexadecenoyl, -octadecenoyl or -icosenoyl, especially 9-cis-octadecenoyl (oleoyl).

In a phospholipid of formula A, n is an integer from two to four, preferably two. The group of the formula —($C_nH_{2n}$)— is unbranched or branched alkylene, for example 1,1-ethylene, 1,1-, 1,2- or 1,3-propylene or 1,2-, 1,3- or 1,4-butylene. 1,2-Ethylene (n=2) is preferred.

Phospholipids of formula A are, for example, naturally occurring cephalins wherein $R_a$, $R_b$ and $R_c$ are hydrogen, or naturally occurring lecithins wherein $R_a$, $R_b$ and $R_c$ are methyl, for example cephalin or lecithin from soybeans, bovine brain, bovine liver or hen's eggs having different or identical acyl groups $R_A$ and $R_B$ or mixtures thereof.

Synthetic, substantially pure phospholipids of formula A having different or identical acyl groups $R_A$ and $R_B$ are preferred.

The term "synthetic" phospholipid of formula A defines phospholipids that have a uniform composition as regards $R_A$ and $R_B$. Such synthetic phospholipids are preferably the lecithins and cephalins defined below, the acyl groups $R_A$ and $R_B$ of which have a defined structure and are derived from a defined fatty acid having a degree of purity higher than approximately 95%. $R_A$ and $R_B$ may be identical or different and may be unsaturated or saturated. $R_A$ is preferably saturated, for example n-hexadecanoyl, and $R_B$ is preferably unsaturated, for example 9-cis-octadecenoyl (=oleoyl).

The term "naturally occurring" phospholipids of formula A defines phospholipids that do not have a uniform composition as regards $R_A$ and $R_B$. Such natural phospholipids are likewise lecithins and cephalins the acyl groups $R_A$ and $R_B$ of which are structurally undefinable and are derived from naturally occurring fatty acid mixtures.

The term "substantially pure" phospholipid defines a degree of purity of more than 70% (by weight) of the phospholipid of formula A, which can be established by suitable determination methods, for example by paper chromatography.

Special preference is given to synthetic, substantially pure phospholipids of formula A wherein $R_A$ is straight-chained $C_{10-20}$alkanoyl having an even number of carbon atoms and $R_B$ is straight-chained $C_{10-20}$alkenoyl having a double bond and an even number of carbon atoms. $R_a$, $R_b$ and $R_c$ are methyl and n is two.

In an especially preferred phospholipid of formula A, $R_A$ is n-dodecanoyl, n-tetradecanoyl, n-hexadecanoyl or n-octadecanoyl and $R_B$ is 9-cis-dodecenoyl, 9-cis-tetradecenoyl, 9-cis-hexadecenoyl, 9-cis-octadecenoyl or 9-cis-icosenoyl. $R_a$, $R_b$ and $R_c$ are methyl and n is two.

A very especially preferred phospholipid of formula A is synthetic 1-n-hexadecanoyl-2-(9-cis-octadecenoyl)-3-sn-phosphatidylcholine having a purity of more than 95%.

Preferred natural, substantially pure phospholipids of formula A are especially lecithin (L-α-phosphatidylcholine) from soybeans or hen's eggs.

The names given in brackets are also customarily used for the acyl radicals in the phospholipids of formula A: 9-cis-dodecenoyl (lauroleoyl), 9-cis-tetradecenoyl (myristoleoyl), 9-cis-hexadecenoyl (palmitoleoyl), 6-cis-octadecenoyl (petroseloyl), 6-trans-octadecenoyl (petroselaldoyl), 9-cis-octadecenoyl (oleoyl), 9-trans-octadecenoyl (elaidoyl), 11-cis-octadecenoyl (vaccenoyl), 9-cis-icosenoyl (gadoleoyl), n-dodecanoyl (lauroyl), n-tetradecanoyl (myristoyl), n-hexadecanoyl (palmitoyl), n-octadecanoyl (stearoyl), n-icosanoyl (arachidoyl).

Other phospholipids are preferably esters of phosphatidic acid (3-sn-phosphatidic acid) with the mentioned acyl radicals, such as phosphatidylserine and phosphatidylethanolamine.

Sparingly soluble active ingredients may also be present in the form of water-soluble, pharmaceutically acceptable salts, as defined above.

The carrier liquid d) comprises the components a), b) and c) or a) and c) as liposomes in such a manner that for a period of from several days up to several weeks no solids or solid aggregates, such as micelles, re-form and the liquid comprising the said components is administrable, preferably orally, if necessary after filtration.

The carrier liquid d) may comprise pharmaceutically acceptable, non-toxic excipients, for example water-soluble excipients that are suitable for producing isotonic conditions, for example ionic additives, such as sodium chloride, or non-ionic additives (structure formers), such as sorbitol, mannitol or glucose, or water-soluble stabilisers for the liposome dispersion, such as lactose, fructose or sucrose.

In addition to the water-soluble excipients, the carrier liquid may comprise emulsifiers, wetting agents or surfactants that can be used for liquid pharmaceutical formulations, especially emulsifiers such as oleic acid, non-ionic surfactants of the fatty acid polyhydroxy alcohol ester type, such as sorbitan monolaurate, monooleate, monostearate or monopalmitate, sorbitan tristearate or trioleate, polyoxyethylene adducts of fatty acid polyhydroxy alcohol esters, such as polyoxyethylene sorbitan monolaurate, monooleate, monostearate, monopalmitate, tristearate or trioleate, polyethylene glycol fatty acid esters, such as polyoxyethyl stearate, polyethylene glycol-400-stearate, polyethylene glycol-2000-stearate, especially ethylene oxide/propylene oxide block polymers of the Pluronic® type (Wyandotte Chem. Corp.) or the Synperonic® type (ICI).

Preferred preservatives are, for example, antioxidants, such as ascorbic acid, or microbicides, such as sorbic acid or benzoic acid.

Ointments are oil-in-water emulsions comprising up to 70%, but preferably 20–50%, water or aqueous phase. Suitable as fatty phase are especially hydrocarbons, for example Vaseline®, paraffin oil or hard paraffins, which, in order to improve the water-binding capacity, preferably comprise suitable hydroxy compounds, such as fatty alcohols or esters thereof, for example cetyl alcohol or wool wax alcohols, such as wool wax. Emulsifiers are corresponding lipophilic substances, such as sorbitan fatty acid esters (Spans®), for example sorbitan oleate and/or sorbitan isostearate. Additives to the aqueous phase are, for example, humectants, such as polyalcohols, for example glycerol, propylene glycol, sorbitol and/or polyethylene glycol, or preservatives and perfumes.

Fatty ointments are anhydrous and comprise as base especially hydrocarbons, for example paraffin, Vaseline® or paraffin oil, also natural or partially synthetic fats, for example coconut fatty acid triglyceride, or preferably hardened oils, for example hydrogenated groundnut oil or castor oil, also fatty acid partial esters of glycerol, for example glycerol mono- and/or di-stearate, and also, for example, the fatty alcohols increasing water-absorption, emulsifiers and/or additives mentioned in connection with the ointments.

Creams are oil-in-water emulsions that comprise more than 50% water. As oily base there are used especially fatty alcohols, for example lauryl, cetyl or stearyl alcohol, fatty acids, for example palmitic or stearic acid, liquid to solid waxes, for example isopropyl myristate, wool wax or beeswax, and/or hydrocarbons, for example Vaseline® (petrolatum) or paraffin oil. Suitable emulsifiers are surface-active substances having predominantly hydrophilic properties, such as corresponding non-ionic emulsifiers, for example fatty acid esters of polyalcohols or ethylene oxide adducts thereof, such as polyglycerol fatty acid esters or polyethylene sorbitan fatty acid esters (Tweens®), and also polyoxyethylene fatty alcohol ethers or fatty acid esters, or corresponding ionic emulsifiers, such as alkali metal salts of fatty alcohol sulfates, for example sodium lauryl sulfate, sodium cetyl sulfate or sodium stearyl sulfate, which are usually used in the presence of fatty alcohols, for example cetyl alcohol or stearyl alcohol. Additives to the aqueous phase are inter alia agents that reduce the drying out of the creams, for example polyalcohols, such as glycerol, sorbitol, propylene glycol and/or polyethylene glycols, and also preservatives and perfumes.

Pastes are creams and ointments having secretion-absorbing powder constituents, such as metal oxides, for example titanium oxide or zinc oxide, also talcum and/or aluminium silicates, the purpose of which is to bind any moisture or secretions present.

Foams are administered from pressurised containers and are liquid oil-in-water emulsions in aerosol form, there being used as propellants halogenated hydrocarbons, such as chlorofluoro-lower alkanes, for example dichlorodifluoromethane and dichlorotetrafluoroethane, or preferably non-halogenated gaseous hydrocarbons, air, $N_2O$ or carbon dioxide. As oil phase there are used inter alia those used above in the sections relating to ointments and creams, and the same applies to the additives mentioned therein.

Tinctures and solutions generally have an aqueous-ethanolic base to which there are added inter alia polyalcohols, for example glycerol, glycols and/or polyethylene glycol, as humectants for reducing evaporation, and fat-restoring substances, such as fatty acid esters with low molecular weight polyethylene glycols, that is to say lipophilic substances that are soluble in the aqueous mixture, as a replacement for the fatty substances removed from the skin by the ethanol, and, if necessary, other excipients and additives.

The pharmaceutical compositions described in the Examples are especially suitable.

The terms used above for the definition of compounds of formula I preferably have the following meanings within the context of this text:

In the description of this invention, the term "lower" used in the definition of groups or radicals, for example lower alkyl, lower alkoxycarbonyl, etc., means that, unless expressly defined to the contrary, the groups or radicals so defined contain up to and including 7 and preferably up to and including 4 carbon atoms.

Asymmetric carbon atoms which may be present in the substituents $R_1$, $B_1$, $R_2$, $R_3$, $A_1$ and/or $A_2$ and in substituted thiomorpholino or morpholino formed by $R_4$ and $R_5$ together with the bonding nitrogen atom, may be in the (R)-, (S)- or (R,S)-configuration. Accordingly, the present compounds may be in the form of isomeric mixtures or pure isomers, especially in the form of diastereoisomeric mixtures, pairs of enantiomers or pure enantiomers.

The general terms and names used in the description of this invention preferably have the following meanings, it being possible in the various categories of definition to use any combinations of or individual radicals from the radicals mentioned hereinabove and hereinbelow instead of the general definitions:

Lower alkoxycarbonyl $R_1$ preferably contains a branched lower alkyl radical, especially a sec- or text-lower alkyl radical, and is, for example, butoxycarbonyl, such as tert-butoxycarbonyl or isobutoxycarbonyl. Tert-butoxycarbonyl is especially preferred.

Heterocyclylcarbonyl $R_1$ contains especially a 5- or 6-membered heterocycle that contains from 1 to 3 hetero atoms selected independently of one another from S, O and N, is unsaturated or fully or partially saturated and is once or up to three times benzo-fused, cyclopenta-, cyclohexa- or cyclohepta-fused, it being possible for the mentioned fused rings to contain a further nitrogen atom as hetero atom, for example a heterocyclyl radical selected from pyrrolyl, furanyl, thienyl, imidazolyl, pyrazolyl, oxazolyl, thiazolyl, pyridyl, pyrazinyl, pyrimidinyl, indolyl, quinolyl, isoquinolyl, quinoxalinyl, β-carbolinyl and a benzo-fused, cyclopenta-, cyclohexa- or cyclohepta-fused derivative of those radicals, which may also be fully or partially saturated, but are preferably partially saturated, or is selected from pyridylcarbonyl, for example pyridyl-3-carbonyl, morpholinylcarbonyl, for example morpholinocarbonyl, and benzofuranoyl, for example 3-benzofuranoyl, and also alternatively or in addition thereto tetrahydroisoquinolylcarbonyl, for example tetrahydroisoquinolyl-3-carbonyl, preferably tetrahydroisoquinolyl-3(S)-carbonyl.

Benzyloxycarbonyl $R_1$ is unsubstituted or substituted by up to three radicals selected independently of one another from fluorine, halo-lower alkyl, for example trifluoromethyl or pentafluoroethyl, lower alkanoyl, such as acetyl, propanoyl, butyryl or pivaloyl, sulfo, lower alkylsulfonyl, for example methylsulfonyl, ethylsulfonyl, n-propylsulfonyl or isopropylsulfonyl, and cyano. Preference is given to benzyloxycarbonyl that is unsubstituted or o-, m- or p-substituted, especially p-substituted, in the phenyl ring by a radical selected from fluorine, trifluoromethyl, sulfo, methylsulfonyl, ethylsulfonyl and cyano, for example benzyloxycarbonyl, fluorophenylmethoxycarbonyl, such as p-fluorophenylmethoxycarbonyl, trifluoromethylphenylmethoxycarbonyl, such as p-trifluoromethylphenylmethoxycarbonyl, methylsulfonylphenylmethoxycarbonyl, such as p-methylsulfonylphenylmethoxycarbonyl, or cyanophenylmethoxycarbonyl, such as p-cyanophenylmethoxycarbonyl.

Heterocyclyloxycarbonyl $R_1$ contains as heterocyclyl especially a 5- or 6-membered heterocycle that contains from 1 to 3 hetero atoms selected independently of one another from S, O and N, is unsaturated or fully or partially saturated and is once or up to three times benzo-fused, cyclopenta-, cyclohexa- or cyclohepta-fused, it being possible for the mentioned fused rings to contain a further nitrogen atom as hetero atom, for example a radical selected from pyrrolyl, thienyl, imidazolyl, pyrazolyl, oxazolyl, thiazolyl, pyrazinyl, pyrimidinyl, indolyl, quinolyl, isoquinolyl, quinoxalinyl, β-carbolinyl and a benzo-fused, cyclopenta-, cyclohexa- or cyclohepta-fused derivative of those radicals, which may also be fully or partially saturated, the heterocyclyl radicals being bonded via a ring carbon atom to the oxygen of the associated oxycarbonyl radical, preferably selected from pyrrolyl, thienyl, imidazolyl, pyrazolyl, oxazolyl, thiazolyl, pyrazinyl, pyrimidinyl, indolyl, quinolyl, isoquinolyl, quinoxalinyl, β-carbolinyl and a fully or partially saturated derivative of those radicals, for example a partially saturated derivative of those radicals or indol-3-yl-oxycarbonyl, benzothiazol-6-yl-oxycarbonyl or quinol-8-yl-oxycarbonyl. In a very especially preferred variant of the definition of $R_1$, the radicals falling under the definition of the substituents heterocyclyloxycarbonyl are not included in all categories of definition.

In the radicals mentioned it is also possible for the bonding carbonyl group to have been replaced by a thiocarbonyl group. A carbonyl group is preferred.

Lower alkylsulfonyl $R_1$ is preferably methylsulfonyl, ethylsulfonyl, n-propylsulfonyl or isopropylsulfonyl. The compounds of formula I wherein $R_1$ is lower alkylsulfonyl and the remaining radicals are as defined may be omitted from the definition of the compounds of formula I, or they are especially preferred.

Heterocyclylsulfonyl preferably contains as heterocyclyl one of the heterocycles mentioned for heterocyclylcarbonyl $R_1$ that is unsubstituted or substituted by lower alkyl, such as methyl or ethyl, preference being given to heterocycles containing at least one nitrogen atom that is bonded to the sulfur atom of the sulfonyl group, and is especially piperidinosulfonyl, or piperazin-1-yl-sulfonyl, pyrrolidin-1-yl-sulfonyl, imidazolidin-1-yl-sulfonyl, pyrimidin-1-yl-sulfonyl, quinolin-1-ylsulfonyl, morpholinosulfonyl or thiomorpholinosulfonyl, especially thiomorpholinosulfonyl or morpholinosulfonyl, that is unsubstituted or substituted by lower alkyl, such as methyl, at the nitrogen atom not bonded to the sulfonyl sulfur atom. The compounds of formula I wherein $R_1$ is heterocyclylsulfonyl and the remaining radicals are as defined may be omitted from the definition of the compounds of formula I, or they are especially preferred.

N-(Heterocyclyl-lower alkyl)-N-lower alkyl-aminocarbonyl $R_1$ contains as heterocyclyl preferably one of the heterocycles mentioned for heterocyclylcarbonyl $R_1$, especially pyridyl, such as 2-, 3- or 4-pyridyl, pyrazinyl, pyrimidinyl, morpholinyl, such as morpholino, thiomorpholinyl, such as thiomorpholino, or quinolyl, such as 2- or 3-quinolyl, and is especially N-(heterocyclylmethyl)-N-methyl-aminocarbonyl, for example N-(pyridylmethyl)-N-methyl-aminocarbonyl, such as N-(2-pyridylmethyl)-N-methyl-aminocarbonyl. The compounds of formula I wherein $R_1$ is N-(heterocyclyl-lower alkyl)-N-lower alkylaminocarbonyl and the remaining radicals are as defined may be omitted from the definition of compounds of formula I, or they are especially preferred.

A bivalent residue $B_1$ of an α-amino acid bonded N-terminally to $R_1$ and C-terminally to the amino group at the carbon atom carrying $R_2$—$CH_2$— is preferably selected from glycine (H-Gly-OH), alanine (H-Ala-OH), valine (H-Val-OH), norvaline (α-aminovaleric acid), leucine (H-Leu-OH), isoleucine (H-Ile-OH), norleucine (α-aminohexanoic acid, H-Nle-OH), serine (H-Ser-OH), homoserine (α-amino-γ-hydroxybutyric acid), threonine (H-Thr-OH), methionine (H-Met-OH), cysteine (H-Cys-OH), proline (H-Pro-OH), trans-3- and trans-4-hydroxyproline, phenylalanine (H-Phe-OH), p-fluorophenylalanine (H-(p-F-Phe)-OH), tyrosine (H-Tyr-OH), p-methoxy-phenylalanine (H-(p-CH$_3$O-Phe)-OH), 4-aminophenylalanine, 4-chlorophenylalanine, 4-carboxyphenylalanine, β-phenylserine (β-hydroxyphenylalanine), phenylglycine, α-naphthylalanine (H-Nal-OH), cyclohexylalanine (H-Cha-OH), cyclohexylglycine, tryptophan (H-Trp-OH), inndoline-2-carboxylic acid, 1,2,3,4-tetrahydroisoquinoline-3-carboxylic acid, aminomalonic acid, aminomalonic acid monoamide, aspartic acid (H-Asp-OH), asparagine (H-Asn-OH), glutamic acid (H-Glu-OH), glutamine (H-Gln-OH), histidine (H-His-OH), arginine (H-Arg-OH), lysine (H-Lys-OH), δ-hydroxylysine, ornithine (α,δ-diaminovaleric acid), α,γ-diaminobutyric acid and α,β-diaminopropionic acid, or alternatively and in addition thereto 4-cyano-phenylalanine (H-(p-CN-Phe)-OH), especially preferably the radical of a hydrophobic amino acid, for example proline, phenylalanine, p-fluorophenylalanine, p-methoxy-phenylalanine, tyrosine, phenylglycine, α-naphthylalanine, cyclohexylalanine, cyclohexylglycine or an aliphatic α-amino acid selected from glycine, valine, norvaline, alanine, leucine, norleucine and isoleucine, especially valine, each of the mentioned α-amino acids being in the D-, L- or (D,L)-form, preferably in the L-form, and being linked especially to radicals $R_1$ selected from lower alkoxycarbonyl, for example tert-butoxycarbonyl, and heterocyclylcarbonyl, for example morpholinocarbonyl.

When $B_1$ is a bond, $R_1$ is bonded directly to the amino nitrogen atom that is bonded to the carbon atom carrying the radical $R_2$—$CH_2$— in formula I.

Phenyl or cyclohexyl $R_2$ or $R_3$ is unsubstituted or substituted by up to three radicals selected independently of one another from hydroxy, lower alkoxy, such as methoxy or ethoxy, halogen, for example fluorine, halo-lower alkyl, for example trifluoromethyl, sulfo, lower alkylsulfonyl, for example methyl- or ethyl-sulfonyl, cyano and nitro, preferably by one or two of those radicals, especially selected from hydroxy, methoxy, fluorine, trifluoromethyl, sulfo, lower alkylsulfonyl, for example methyl- or ethyl-sulfonyl, and cyano, and in the case of phenyl selected very especially from fluorine and cyano, and in the case of cyclohexyl very especially from fluorine, trifluoromethyl, sulfo and lower alkylsulfonyl, more especially fluorine; the mentioned substituents are bonded in the 2-, 3- or 4-position of the phenyl or cyclohexyl ring, especially in the 4-position, such as in phenyl, cyclohexyl, 4-fluoro- or 4-cyano-phenyl or 4-fluorocyclohexyl, especially in phenyl, cyclohexyl, 4-cyanophenyl or 4-fluorophenyl.

Especially preferred are those combinations of $R_2$ and $R_3$ in which at least one of the radicals $R_2$ and $R_3$ is substituted by one or up to three radicals selected from halogen, especially fluorine, halo-lower alkyl, especially trifluoromethyl, sulfo, lower alkylsulfonyl, especially methyl- or ethyl-sulfonyl, cyano and nitro, one substituent being very especially selected from fluorine and cyano.

More especially $R_2$ is selected from phenyl, 4-hydroxyphenyl, 4-methoxyphenyl, 4-fluorophenyl, cyclohexyl and 4-trifluoromethylphenyl, while $R_3$ is selected from phenyl, 4-hydroxyphenyl, 4-methoxyphenyl, cyclohexyl, 4-fluorophenyl, 4-trifluoromethylphenyl and 4-cyanophenyl.

Very especially $R_2$ is selected from phenyl, 4-fluorophenyl and cyclohexyl, while $R_3$ is selected from phenyl, cyclohexyl, 4-fluorophenyl, 4-methoxyphenyl and 4-cyanophenyl.

Greatest preference is given to the combinations: $R_2$ phenyl and $R_3$ phenyl; $R_2$ cyclohexyl and $R_3$ 4-cyanophenyl; $R_2$ cyclohexyl and $R_3$ 4-fluorophenyl; and $R_2$ and $R_3$ each cyclohexyl. Alternatively or in addition thereto, greatest preference is given also to the combinations $R_2$ phenyl and $R_3$ 4-fluorophenyl; $R_2$ phenyl and $R_3$ 4-cyanophenyl; $R_2$ 4-fluorophenyl and $R_3$ 4-fluorophenyl; $R_2$ 4-fluorophenyl and $R_3$ 4-trifluoromethylphenyl; $R_2$ 4-trifluoromethylphenyl and $R_3$ phenyl; $R_2$ 4-trifluoromethylphenyl and $R_3$ 4-fluorophenyl; $R_2$ 4-trifluoromethylphenyl and $R_3$ 4-trifluoromethylphenyl; $R_2$ hydroxyphenyl and $R_3$ phenyl; $R_2$ phenyl and $R_3$ hydroxyphenyl; $R_2$ phenyl and $R_3$ 4-methoxyphenyl; $R_2$ hydroxyphenyl and $R_3$ hydroxyphenyl; and $R_2$ cyclohexyl and $R_3$ 4-methoxyphenyl.

Hydroxy groups, especially the hydroxy group in compounds of formula I at the carbon atom adjacent to the carbon atom carrying the radical $R_2$—$CH_2$—, may be free or in protected form, especially free or protected in the form of a physiologically cleavable ester, for example in the form of lower alkanoyloxy, such as acetyloxy. The last-mentioned hydroxy group is preferably free.

A bivalent residue of an α-amino acid $A_1$ bonded N-terminally to the group —C═O and C-terminally to $A_2$ is, for example, one of the α-amino acids mentioned above for $B_1$, it being possible for those amino acids to be in the (D)-, (L)- or (D,L)-form, preferably in the (D)- or (L)-form, especially in the (L)-form. Preference is given to the hydrophobic α-amino acids, especially the aliphatic hydrophobic α-amino acids, mentioned for $B_1$, for example glycine, valine or isoleucine. In the mentioned α-amino acids the carboxy group bonded to $A_2$ is not reduced or is reduced, especially to a methylene group, for example in the mentioned hydrophobic α-amino acids, such as in the reduced amino acid residues Gly(red), Val(red) or Ile(red), especially in Val(red), the suffix (red) indicating the reduction of the carbonyl group of the corresponding amino acid residue to the methylene group.

When $A_1$ is a bond, $A_2$ is bonded directly to the carbonyl group at the carbon atom carrying the radical $R_3$—$CH_2$—.

A bivalent residue of an α-amino acid $A_2$ bonded N-terminally to $A_1$ and C-terminally to the group $NR_4R_5$ is, for example, one of the α-amino acids mentioned above for $B_1$, it being possible for those amino acids to be in the (D)-, (L)- or (D,L)-form, preferably in the (D)- or (L)-form, especially in the (L)-form. Preference is given to the hydrophobic α-amino acids mentioned for $B_1$, for example glycine, valine, phenylalanine, p-fluorophenylalanine, tyrosine, p-methoxy-phenylalanine, phenylglycine, α-naphthylalanine, cyclohexylalanine or cyclohexylglycine, preferably glycine, valine, phenylalanine, p-fluorophenylalanine, p-methoxy-phenylalanine or cyclohexylalanine, the mentioned residues being in the (D)- or (L)-form, but preferably in the (L)-form with the exception of phenylalanine which is in the (L)- or the (D)-form.

A bivalent residue of a dipeptide, formed by $A_1$ and $A_2$, the central peptide bond of which has been reduced and which is bonded N-terminally to the group —C═O and C-terminally to the group $NR_4R_5$ preferably consists of two of the above-mentioned hydrophobic α-amino acids, especially an N-terminal amino acid residue selected from Gly(red), Val(red) and Ile(red) and a C-terminal amino acid selected from glycine, phenylalanine, tyrosine, p-methoxyphenylalanine, cyclohexylalanine and p-fluorophenylalanine.

Especially preferably $A_1$ and $A_2$ together form a bivalent residue of a dipeptide of the formula Val-Phe, Ile-Phe, Val-Cha, Ile-Cha, Val-Gly, Val-(p-F-Phe), Val-(p-$CH_3$O-Phe), Gly-(p-F-Phe); and alternatively or additionally the residue of a dipeptide of the formula Val-Tyr, Ile-Tyr, Gly-Tyr, Ile-Gly or Val-Val; wherein the amino acids are in the (D)- or (L)-form, especially in the (L)-form, with the exception of (L)-Val-Phe in which Phe is in the (L)- or (D)-form, or a derivative thereof having a reduced central amide bond, for example of the formula Val(red)-Phe, bonded N-terminally to the group —C═O and C-terminally to the group $NR_4R_5$.

A preferred form of the invention relates either to compounds of formula I wherein $B_1$ is one of the mentioned bivalent residues of an α-amino acid and one of the radicals $A_1$ and $A_2$ is a bond and the other is one of the mentioned α-amino acids, or to compounds of formula I wherein $B_1$ is a bond and $A_1$ and $A_2$ are each one of the mentioned bivalent residues of an α-amino acid or together form one of the mentioned bivalent residues of a dipeptide having a reduced central amide bond.

Thiomorpholino or morpholino formed by $R_4$ and $R_5$ together with the bonding nitrogen atom is unsubstituted or substituted at one or more of the carbon atoms, preferably at one carbon atom, by lower alkyl, such as ethyl, propyl, butyl, isobutyl or tert-butyl, by phenyl- or naphthyl-lower alkyl, such as benzyl, 1- or 2-naphthylmethyl or phenyl-1- or phenyl-2-ethyl, especially phenyl-1- or phenyl-2-ethyl, by hydroxy, by lower alkoxy, such as methoxy, ethoxy or tert-butoxy, by amino, by lower alkylamino, such as methyl- or ethylamino, or by di-lower alkylamino, such as dimethylamino or diethylamino, by lower alkanoyl, such as acetyl or propionyl, by phenyl- or naphthyl-lower alkanoyl, such as phenylacetyl or 1- or 2-naphthylacetyl, by carboxy, by lower alkoxycarbonyl, such as isopropoxycarbonyl or tert-butoxycarbonyl, by phenyl-, naphthyl- or fluorenyl-lower alkoxycarbonyl, such as benzyloxycarbonyl, 1- or 2-naphthylmethoxycarbonyl or 9-fluorenylmethoxycarbonyl, by carbamoyl, by mono- or di-lower alkylcarbamoyl, such as dimethylcarbamoyl, by mono- or di-hydroxy-lower alkyl-carbamoyl, such as di-hydroxymethylcarbamoyl, by sulfo, by lower alkylsulfonyl, such as methylsulfonyl or ethylsulfonyl, by phenyl- or naphthyl-sulfonyl, wherein phenyl may be substituted by lower alkyl, for example methyl or ethyl, for example phenylsulfonyl or toluenesulfonyl, by sulfamoyl, by halogen, for example fluorine or chlorine, by cyano, by nitro and/or by oxo.

Very preferably $R_4$ and $R_5$ together with the bonding nitrogen atom form unsubstituted thiomorpholino or morpholino, especially unsubstituted morpholino.

Salts of inhibitors of HIV aspartate proteases, especially of compounds of formula I, are especially acid addition salts, salts with bases or, where several salt-forming groups are present, optionally also mixed salts or internal salts.

Salts are especially the pharmaceutically acceptable, non-toxic salts, especially of compounds of formula I.

Such salts are formed, for example, by inhibitors of HIV aspartate proteases, especially compounds of formula I having an acidic group, for example a carboxy or sulfo group, and are, for example, the salts thereof with suitable bases, such as non-toxic metal salts derived from metals of groups Ia, Ib, IIa and IIb of the Periodic Table of Elements, especially suitable alkali metal salts, for example lithium, sodium or potassium salts, or alkaline earth metal salts, for example magnesium or calcium salts, and also zinc salts or ammonium salts, as well as those salts which are formed with organic amines, such as unsubstituted or hydroxy-substituted mono-, di- or tri-alkylamines, especially mono-, di- or tri-lower alkylamines, or with quaternary ammonium compounds, for example with N-methyl-N-ethylamine, diethylamine, triethylamine, mono-, bis- or tris-(2-hydroxy-lower alkyl)-amines, such as mono-, bis- or tris-(2-hydroxyethyl)-amine, 2-hydroxy-tert-butylamine or tris (hydroxymethyl)methylamine, N,N-di-lower alkyl-N-(hydroxy-lower alkyl)amines, such as N,N-dimethyl-N-(2-hydroxyethyl)-amine or tri(2-hydroxyethyl)amine, N-methyl-D-glucamine or quaternary ammonium salts, such as tetrabutylammonium salts. The compounds of formula I having a basic group, for example an amino group, may form acid addition salts, for example with inorganic acids, for example a hydrohalic acid, such as hydrochloric acid, sulfuric acid or phosphoric acid, or with organic carboxylic, sulfonic, sulfo or phospho acids or N-substituted sulfamic acids, for example acetic acid, propionic acid, glycolic acid, succinic acid, maleic acid, hydroxymaleic acid, methylmaleic acid, fumaric acid, malic acid, tartaric acid, gluconic acid, glucaric acid, glucuronic acid, citric acid, benzoic acid, cinnamic acid, mandelic acid, salicylic acid, 4-aminosalicylic acid, 2-phenoxybenzoic acid, 2-acetoxybenzoic acid, embonic acid, nicotinic acid or isonicotinic acid, and also with amino acids, for example the α-amino acids mentioned above, and with methanesulfonic acid, ethanesulfonic acid, 2-hydroxyethanesulfonic acid, ethane-1,2-disulfonic acid, benzenesulfonic acid, 4-methylbenzenesulfonic acid, naphthalene-2-sulfonic acid, 2- or 3-phosphoglycerate, glucose-6-phosphate, N-cyclohexylsulfamic acid (with the formation of cyclamates) or with other acidic organic compounds, such as ascorbic acid. Compounds of formula I having acidic and basic groups may also form internal salts.

For the purposes of isolation and purification at intermediate stages, for example in the preparation of pharmaceutical compositions, it is also possible to use pharmaceutically unacceptable salts.

The terms "compounds" and "salts" include expressly also individual compounds and individual salts.

Hereinabove and hereinbelow, any reference made to inhibitors of HIV aspartate proteases, especially of formula I (and also as "active substances", "compounds", etc) is intended to include, where appropriate and expedient, the corresponding pharmaceutically acceptable salts where salt-forming groups are present.

The invention relates preferably to pharmaceutical compositions comprising compounds of formula I or the use or a process or a method for treatment by the administration of compounds of formula I wherein $R_1$ is hydrogen, tert-butoxycarbonyl, isobutyloxycarbonyl, pyridine-3-carbonyl, morpholinocarbonyl, 3-benzofuranoyl, 1,2,3,4-tetrahydro-isoquinoline-3-carbonyl, benzyloxycarbonyl substituted by up to three radicals selected independently of one another from fluorine, halo-lower alkyl, lower alkanoyl, sulfo, lower alkylsulfonyl and cyano, or heterocyclyloxycarbonyl wherein heterocyclyl is bonded via a carbon atom and is selected from pyrrolyl, thienyl, imidazolyl, pyrazolyl, oxazolyl, thiazolyl, pyrazinyl, pyrimidinyl, indolyl, quinolyl, isoquinolyl, quinoxalinyl, β-carbolinyl and a fully or partially saturated derivative of those radicals, or wherein heterocyclyloxycarbonyl is absent as a definition of $R_1$, $B_1$ is a bond or a bivalent residue of an α-amino acid bonded N-terminally to $R_1$ and C-terminally to the amino group at the carbon atom carrying $R_2$—$CH_2$—, preferably the radical of a hydrophobic amino acid, for example proline, phenylalanine, p-fluorophenylalanine, phenylglycine, α-naphthylalanine, cyclohexylalanine, cyclohexylglycine or an aliphatic α-amino acid selected from glycine, valine, norvaline, alanine, leucine, norleucine and isoleucine, especially valine, each of the mentioned α-amino acids preferably being in the D-, L- or (D,L)-form, especially in the L-form, and each of the mentioned amino acids preferably being substituted by one of the radicals mentioned under $R_1$ selected from hydrogen, N-tert-butoxycarbonyl and morpholinocarbonyl, $R_2$ and $R_3$ are each independently of the other phenyl or cyclohexyl, those radicals being unsubstituted or substituted by one or two radicals selected independently of one another from hydroxy, methoxy, fluorine, sulfo, lower alkylsulfonyl, trifluoromethyl and cyano, as indicated above in the general definitions, $A_1$ is a bivalent residue of a hydrophobic α-amino acid, as indicated above under the general definitions, bonded N-terminally to the group —C=O and C-terminally to $A_2$, $A_2$ is a bivalent residue of a hydrophobic α-amino acid, preferably as defined above under the general definitions, bonded N-terminally to $A_1$ and C-terminally to the radical $NR_4R_5$, the said amino acid residues being in the (D)- or (L)-form, preferably in the (L)-form, with the exception of phenylalanine which is in the (L)- or the (D)-form, especially $A_1$ and $A_2$ form a bivalent residue of a dipeptide of the formula Val-Phe, Ile-Phe, Val-Cha, Ile-Cha, Ile-Gly, Val-Val, Val-Gly, Val-(p-F-Phe), Val-Tyr, Val-(p-CH$_3$O-Phe) or Gly-(p-F-Phe), wherein the amino acids are in the (D)- or (L)-form, especially in the (L)-form, with the exception of (L)-Val-Phe in which Phe is in the (L)- or (D)-form; or $A_1$ and $A_2$ together form a bivalent residue of a dipeptide consisting of two hydrophobic α-amino acids, preferably two of those mentioned above under the general definitions, the central amide bond of which has been reduced and which is bonded N-terminally to the group —C=O and C-terminally to the group $NR_4R_5$, as indicated in the general definitions, for example having the formula Val(red)-Phe, and $R_4$ and $R_5$ together with the bonding nitrogen atom form thiomorpholino or morpholino, especially morpholino, and alternatively or in addition thereto the compounds of formula I wherein $R_1$ is morpholinosulfonyl or N-(2-pyridylmethyl)-N-methylaminocarbonyl and the remaining radicals are as defined; and pharmaceutically acceptable salts of those compounds where salt-forming groups are present, the hydroxy group in compounds of formula I at the carbon atom adjacent to the carbon atom carrying the radical $R_2$—$CH_2$— being in free form or protected by lower alkanoyl, especially in free form; and in the definition of $R_1$ heterocyclyloxycarbonyl may also be omitted.

The present invention relates especially to pharmaceutical compositions comprising compounds of formula I or the use or a process or a method for treatment by the administration of compounds of formula I wherein $R_1$ is hydrogen, tert-butoxycarbonyl, isobutyloxycarbonyl, pyridine-3-carbonyl, morpholinocarbonyl, 3-benzofuranoyl or 1,2,3,4-tetrahydro-isoquinoline-3-carbonyl, or alternatively or in addition thereto morpholinosulfonyl or N-(2-pyridylmethyl)-N-methylaminocarbonyl, $B_1$ is a bond or a bivalent residue of the α-amino acid valine bonded N-terminally to $R_1$ and C-terminally to the amino group at the carbon atom carrying $R_2$—$CH_2$—, $R_1$ in the latter case preferably being hydrogen, tert-butoxycarbonyl or morpholinocarbonyl or alternatively or in addition thereto morpholinosulfonyl or N-(2-pyridylmethyl)-N-methyl-aminocarbonyl, $R_2$ and $R_3$ are each independently of the other phenyl or cyclohexyl, those radicals being unsubstituted or substituted by one or two radicals selected independently of one another from hydroxy, methoxy, fluorine and cyano, especially by one of the said radicals, preferably in the 4-position, for example as in 4-hydroxyphenyl, 4-methoxyphenyl, 4-fluorophenyl, 4-cyanophenyl or 4-fluorocyclohexyl, such as in the combinations of $R_2$ and $R_3$ mentioned as being especially preferred under the general definitions above, or alternatively or in addition thereto $R_2$ and $R_3$ are each independently of the other phenyl or cyclohexyl which is unsubstituted or substituted by one or two radicals selected independently of one another from trifluoromethyl, cyano and fluorine, especially by one of those radicals, preferably in the 4-position, for example as in 4-trifluoromethylphenyl, 4-cyanophenyl or 4-fluorophenyl, $A_1$ and $A_2$ together form a bivalent residue of a dipeptide of the formula Val-Phe, Ile-Phe, Val-Cha, Ile-Cha, Ile-Gly, Val-Val, Val-Gly, Val-(p-F-Phe), Val-Tyr, Val-(p-$CH_3O$-Phe), Gly-(p-F-Phe) or a derivative thereof having a reduced central amide bond of the formula Val(red)-Phe, bonded N-terminally to the group —C=O and C-terminally to the group $NR_4R_5$, and $R_4$ and $R_5$ together with the bonding nitrogen atom are thiomorpholino or morpholino, especially morpholino, and pharmaceutically acceptable salts of those compounds where salt-forming groups are present, the hydroxy group in compounds of formula I at the carbon atom adjacent to the carbon atom carrying the radical $R_2$—$CH_2$— being free or being protected by acetyl; both the free compounds of formula I and the protected form wherein all other radicals are as defined, or salts thereof, being especially preferred.

Great importance is attached to pharmaceutical compositions comprising compounds of formula I or the use or a process or a method for treatment by the administration of a compound of formula I wherein $R_1$ is lower alkoxycarbonyl, especially secondary or tertiary lower alkoxycarbonyl or methoxycarbonyl, $B_1$ is a bond, $R_2$ and $R_3$ are phenyl, $A_1$ is valyl, especially (L)-valyl, $A_2$ is phenylalanyl, especially (L)-phenylalanyl, and $R_4$ and $R_5$ together with the bonding nitrogen atom are morpholino.

Very great importance is attached to pharmaceutical compositions comprising compounds of formula I or the use or a process or a method for treatment by the administration of a compound of formula I wherein $R_1$ is tert-butoxycarbonyl, $B_1$ is a bond, $R_2$ and $R_3$ are phenyl, $A_1$ is valyl, especially (L)-valyl, $A_2$ is phenylalanyl, especially (L)-phenylalanyl, and $R_4$ and $R_5$ together with the bonding nitrogen atom are morpholino.

Very great importance is attached to pharmaceutical compositions comprising compounds of formula I or the use or a process or a method for treatment by the administration of a compound of formula I wherein $R_1$ is tert-butoxycarbonyl, $B_1$ is a bond, $R_2$ is phenyl, $R_3$ is 4-methoxyphenyl, $A_1$ is valyl, especially (L)-valyl, $A_2$ is phenylalanyl, especially (L)-phenylalanyl, and $R_4$ and $R_5$ together with the bonding nitrogen atom are morpholino.

Very great importance is attached to pharmaceutical compositions comprising compounds of formula I or the use or a process or a method for treatment by the administration of a compound of formula I wherein $R_1$ is tert-butoxycarbonyl, $B_1$ is a bond, $R_2$ is cyclohexyl, $R_3$ is 4-methoxyphenyl, $A_1$ is valyl, especially (L)-valyl, $A_2$ is phenylalanyl, especially (L)-phenylalanyl, and $R_4$ and $R_5$ together with the bonding nitrogen atom are morpholino.

Greatest importance is attached to pharmaceutical compositions comprising compounds of formula I or the use or a process or a method for treatment by the administration of the compounds of formula I mentioned in the Examples, preferably under the conditions mentioned therein.

The following Examples serve to illustrate the invention but do not limit the scope thereof in any way:

Temperatures are given in degrees Celsius (°C.). Where no temperature is specified, the reaction takes place at room temperature. The $R_f$ values, which indicate the ratio of the seepage propagation of the substance in question to the seepage propagation of the eluant front, are determined on thin-layer silica gel plates by thin-layer chromatography (TLC) in the following solvent systems:

TLC eluant systems:

| A | hexane/ethyl acetate | 1:1 |
| B | ethyl acetate | — |
| C | hexane/ethyl acetate | 4:1 |
| D | hexane/ethyl acetate | 2:1 |
| E | hexane/ethyl acetate | 3:1 |
| F | methylene chloride/methanol | 9:1 |
| G | chloroform/methanol/water/glacial acetic acid | 85:13:1.5:0.5 |
| H | hexane/ethyl acetate | 1:2 |

The abbreviation "$R_f(B)$", for example, indicates that the $R_f$ value was determined in solvent system B. The quantitative ratio of solvents to one another is always given in parts by volume (v/v). In the definition of the eluant systems for column chromatography, the quantitative ratios of the solvents used are also given in parts by volume (v/v).

The other short names and abbreviations used have the following meanings:

| Boc | tert-butoxycarbonyl |
| BOP | benzotriazol-1-yloxy-tris(dimethyl-amino)phosphonium hexafluorophosphate |
| brine | saturated sodium chloride solution |
| DCC | dicyclohexylcarbodiimide |
| DEPC | diethyl pyrocarboxylate |
| DMF | dimethylformamide |
| DMSO | dimethyl sulfoxide |
| ether | diethyl ether |
| FAB-MS | Fast-Atom-Bombardment mass spectroscopy |
| h | hour(s) |
| HOBt | 1-hydroxybenzotriazole |
| IR | infrared spectroscopy |
| min | minute(s) |
| org. | organic |
| m.p. | melting point |
| Pd/C | palladium on activated carbon (catalyst) |
| TBAF | tetrabutylammonium fluoride (trihydrate) |
| TFA | trifluoroacetic acid |
| THF | tetrahydrofuran |
| TLC | thin-layer chromatography |
| Z | benzyloxycarbonyl |

Mass spectroscopic data are obtained according to the Fast-Atom-Bombardment (FAB-MS) method. The mass data relate to the protonated molecule ion $(M+H)^+$.

The values for the IR spectra are given in $cm^{-1}$, with the solvent in question being indicated in round brackets.

The abbreviations customary in peptide chemistry are used to denote bivalent residues of natural α-amino acids.

The configuration at the α-carbon atom is indicated by the prefix (L)- or (D)-.
HPLC gradients:

| | |
|---|---|
| I | 20% → 100% a) in b) for 20 min. |
| II | 20% → 100% a) in b) for 35 min. |
| III | 20% → 100% a) in b) for 20 min + 100% a) for 8 min. |

Eluant a): acetonitrile+0.05% TFA; eluant b): water+ 0.05% TFA. Column (250×4.6 mm) filled with Reversed-Phase material $C_{18}$-Nucleosil® (5 μm mean particle size, silica gel covalently derivatised with octadecylsilanes, Macherey & Nagel, Düren, Federal Republic of Germany). Detection by UV absorption at 215 nm. The retention times ($t_{Ret}$) are given in minutes. Flow rate 1 ml/min.

The residue with the short name -Phe[C]Phe- denotes the bivalent residue of 5(S)-amino-2(R)-benzyl-4(S)-hydroxy-6-phenylhexanoic acid and has the formula

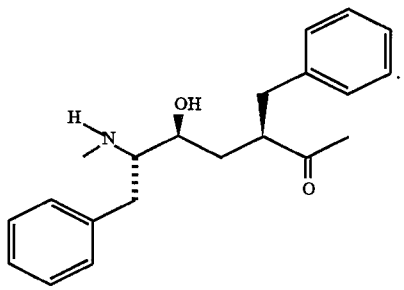

Analogously, the radical -Phe[C](p-$CH_3$O)Phe- is the bivalent residue of 5(S)-amino-4(S)-hydroxy-2(R)-4-methoxybenzyl-6-phenyl-hexanoic acid, a 2-(4-methoxyphenyl)-methyl radical replacing the 2-phenylmethyl radical in the formula last given.

EXAMPLE 1

Boc-Phe[C]Phe-(L)-Val-(L)-Phe-morpholin-4-ylamide 247.2 mg of TBAF are added to a solution of 330.3 mg of 5(S)-Boc-amino-4(S)-(tert-butyldimethylsilyloxy)-6-phenyl-2(R)-phenylmethyl-hexanoyl-(L)-Val-(L)-Phe-morpholin-4-ylamide in 3 ml of absolute DMF and the reaction mixture is then stirred for 4.5 hours at room temperature. The colourless solution is poured onto 50 ml of water and extracted four times with ethyl acetate. The combined extracts are washed twice using 25 ml of sodium hydrogen carbonate solution each time, twice with water and once with brine and then dried over sodium sulfate. After evaporation of the solvent, the residue is crystallised from hexane and the title compound is obtained. TLC $R_f$(B)=0.5; FAB-MS $(M+H)^+$=729.

The starting material is prepared as follows:

1 a) N-3(S)-(Boc-amino)-2(R,S)-hydroxy-4-phenyl-1-trimethylsilyl-butane 24.7 g of magnesium are placed in 100 ml of absolute ether, and then over a period of 35 minutes a small amount of iodine and, at the same time, 132.5 ml of chloromethyl-trimethylsilane and 300 ml of ether are added thereto, the temperature being maintained at 38° C. by means of an ice bath. The resulting reaction mixture is then stirred for 1.5 hours at room temperature. After cooling to −60° C., a suspension of 48.6 g of N-Boc-phenylalaninal (preparation: D. J. Kempf, J. Org. Chem. 51, 3921 (1986)) in 1.1 liters of ether is added in the course of 40 minutes. The reaction mixture is heated to room temperature over a period of 90 minutes and then stirred at that temperature for a further 90 minutes, then poured onto 2 liters of ice-water and 1.5 liters of 10% aqueous citric acid. The separated aqueous phase is extracted twice with 500 ml of ether. All the ether extracts are washed with 500 ml of a 10% citric acid solution and twice with brine. After drying over sodium sulfate, concentration is carried out in vacuo and the resulting title compound is used further without additional purification. TLC $R_f$(C)=0.6; FAB-MS $(M+H)^+$=338.

1 b) 1-Phenyl-3-buten-2(S)-amine

At 5° C., 35.6 ml of an approximately 48% solution of boron trifluoride ethyl etherate are added in the course of 10 minutes to a solution of 18.8 g of N-3(S)-(Boc-amino)-2-(R,S)-hydroxy-4-phenyl-1-trimethylsilyl-butane in 420 ml of methylene chloride. The reaction mixture is then stirred at room temperature for 16 hours, cooled to 10° C., and in the course of 20 minutes 276 ml of a 4N sodium hydroxide solution are added. The aqueous phase is separated off and extracted twice using 400 ml of methylene chloride each time. The combined organic extracts are washed with brine and dried over sodium sulfate. The title product is used further without additional purification. TLC $R_f$(G)=0.15; IR (methylene chloride) ($cm^{-1}$): 3370, 3020, 2920, 1640, 1605.

1 c) N-Boc-1-phenyl-3-buten-2(S)-amine 21.5 g of 1-phenyl-3-buten-2(S)-amine are dissolved in 500 ml of absolute methylene chloride, and a solution of 38.3 g of Boc anhydride in 250 ml of methylene chloride is added dropwise thereto. After being stirred at room temperature for 1.5 hours, the reaction mixture is concentrated to 100 ml, then diluted with 1.5 liters of ether and washed in succession twice with 400 ml of 10% citric acid, once with 400 ml of water, once with 400 ml of saturated aqueous sodium hydrogen carbonate solution and twice with brine and dried over sodium sulfate. After evaporation of the solvent, purification is carried out by chromatography ($SiO_2$, hexane/ethyl acetate: 95/5 to 80/20) and the title compound is crystallised from hexane. M.p. 67°–68° C.; TLC $R_f$(C)=0.4; FAB-MS $(M+H)^+$=248.

1 d) 2(R)-[1(S)-(Boc-amino)-2-phenylethyl]-oxirane

A solution of 9.74 g of m-chloroperbenzoic acid in 50 ml of methylene chloride is added in the course of 15 minutes at 0°–5° C. to a solution of 1.45 g of N-Boc-1-phenyl-3-buten-2(S)-amine in 20 ml of methylene chloride. After being stirred for 18 hours at the same temperature, the reaction mixture is stirred to complete the reaction for a further 8 hours with heating at room temperature and then poured onto ice-cold 10% sodium carbonate solution. The aqueous phase is extracted three times with ether. The combined organic phases are washed in succession three times with 10% sodium sulfite solution, three times with saturated sodium hydrogen carbonate solution, with sodium thiosulfate solution and brine and dried over sodium sulfate. After evaporation of the solvent, the title compound is purified by column chromatography ($SiO_2$, hexane/ethyl acetate: 4/1) and crystallised from hexane. M.p. 51°–52° C.; TLC $R_f$(C)=0.33; FAB-MS $(M+H)^+$=264.

1 e) 5(S)-[1(S)-(Boc-amino)-2-phenylethyl]-3(R,S)-carbethoxy-dihydrofuran-2-(3H)-one 3.4 g of sodium are added in portions to a solution of 26 ml of malonic acid diethyl ester in 260 ml of absolute ethanol. When the sodium has been consumed (about 1.5 hours), a solution of 13 g of 2(R)-[1(S)-(Boc-amino)-2-phenylethyl]-oxirane in 100 ml of ethanol is added dropwise in the course of 10 minutes. After being stirred for 5 hours at room temperature, the reaction mixture is poured onto 1.5 liters of ice-water and adjusted to pH 4 with 10% citric acid.

After extraction four times with ether, the combined organic phases are washed in succession twice with saturated aqueous sodium hydrogen carbonate solution, once with brine, again with saturated aqueous sodium hydrogen carbonate solution, with water and again with brine. After evaporation of the solvent, the title compound is obtained by column chromatography (SiO$_2$, hexane/ethyl acetate: 4/1). TLC R$_f$ (C)=0.22; FAB-MS (M+H)$^+$=378.

1 f) 5(S)-[(1(S)-(Boc-amino)-2-phenylethyl]-3(R,S)-carbethoxy-3-phenylmethyl-dihydrofuran-2-(3H)-one A solution of 23.8 g of 5(S)-[1(S)-(Boc-amino)-2-phenylethyl]-3(R,S)-carbethoxy-dihydrofuran-2-(3H)-one in 410 ml of absolute ethanol and 14.4 ml of benzyl bromide is added to a solution of 2.76 g of sodium in 410 ml of absolute ethanol. The reaction mixture is stirred at room temperature under argon for 18 hours and then poured onto a mixture of ice and 10% citric acid. After extraction three times with ether, the combined organic extracts are washed with water and brine and dried over sodium sulfate. After concentration there is obtained the title compound in the form of a colourless oil which is used in the next step without additional purification. TLC R$_f$ (C)=0.4; FAB-MS (M+H)$^+$=468.

1 g) 5(S)-[1(S)-(Boc-amino)-2-phenylethyl]-3(R)-phenylmethyl-dihydrofuran-2-(3H)-one and 5(S)-[1(S)-(Boc-amino)-2-phenylethyl]-3(S)-phenylmethyl-dihydrofuran-2-(3H)-one 81.4 ml of a 1M aqueous lithium hydroxide solution are added dropwise at room temperature over a period of 5 minutes to a solution of 10 g of 5(S)-[(1(S)-(Boc-amino)-2-phenylethyl]-3(R,S)-carbethoxy-3-phenylmethyl-dihydrofuran-2-(3H)-one in 175 ml of dimethoxyethane. The reaction mixture is then stirred for 15 hours at room temperature and after evaporation of the solvent the resulting residue is poured onto 500 ml of 10% citric acid and extracted three times with ether. The combined ether phases are washed once with brine and dried over sodium sulfate. After evaporation of the solvent there are obtained 9.8 g of the crude carboxylic acid which is decarboxylated by heating for 14 hours at 90° C. in 450 ml of toluene to form the title product. That product is purified by column chromatography (hexane/ethyl acetate: 9/1), there being obtained first 5(S)-[1(S)-(Boc-amino)-2-phenylethyl]-3(R)-phenylmethyl-dihydrofuran-2-(3H)-one [TLC R$_f$ (C)=0.3; FAB-MS (M+H)$^+$=396] and subsequently 5(S)-[1(S)-(Boc-amino)-2-phenylethyl]-3(S)-phenylmethyl-dihydrofuran-2-(3H)-one [TLC R$_f$ (C)=0.25; FAB-MS (M+H)$^+$=396].

[Alternative synthesis for 5(S)-[1(S)-(Boc-amino)-2-phenylethyl]-3(R)-phenylmethyl-dihydrofuran-2-(3H)-one, which is also suitable for relatively large amounts:

α) 5(S)-[1(S)-(Boc-amino)-2-phenylethyl]-dihydrofuran-2-(3H)-one (A. E. DeCamp, A. T. Kawaguchi, R. P. Volante, and I. Shinkai, Tetrahedron Lett. 32, 1867 (1991)). Under a nitrogen atmosphere, 173 g of Zn/Cu (preparation: R. D. Smith, H. E. Simmons, W. E. Parham, M. D. Bhavsar, Org. Synth., Coll. Vol 5, 855 (1973)) and 280 ml of dimethylacetamide are added to a solution of 375 g (1.65 mol) of 3-iodopropionic acid ethyl ester [preparation: a suspension of 170 ml of 2-bromopropionic acid ethyl ester (Fluka; Buchs, Switzerland) and 950 g of sodium iodide in 1.8 liters of acetone is filtered, the filtrate is partially concentrated by evaporation, poured onto about 2.5 liters of ether, washed with 1.0 liter of 1% sodium thiosulfate solution and finally with brine, dried with sodium sulfate and concentrated by evaporation. Distillation (83° C.; 20 mbar) yields the pure 3-iodopropionic acid ethyl ester: MS (M)$^+$=228; $^1$H-NMR (200 MHz, CDCl$_3$): 4.17 (q, 7 Hz, 2 H); 3.34 and 2.97 (2t, 7 Hz, 2×2 H); 1.28 (t, 7 Hz, 3 H)] in 1700 ml of toluene and the mixture is stirred vigorously for 1 hour at room temperature and for 4 hours at 80° C. (→zinc homoenolate solution). In a second apparatus (nitrogen atmosphere), 127 ml (1.14 mol) of titanium tetrachloride are added to a solution of 122 ml (0.40 mol) of tetraisopropyl orthotitanate in 350 ml of toluene and 1900 ml of methylene chloride with slight cooling at an internal temperature of from 15° to 25° C., and the mixture is then stirred for 15 minutes at room temperature (→yellow solution) and cooled to −40° C. (→partial crystallisation of the trichlorotitanium isopropanolate). The zinc homoenolate solution, which has cooled to room temperature, is filtered under an argon atmosphere through a G3 fritted glass filter and added dropwise to the trichlorotitanium isopropanolate, the temperature being maintained at −30° C. to −25° C. (→deep-red solution), and the solution is stirred for 5 minutes at −25° C. and cooled to −40° C. A solution of 233 g (0.85 mol) of N-Boc-phenylalaninal (preparation: D. J. Kempf, J. Org. Chem. 51, 3921 (1986), then crystallisation from hexane (0° C., about 18 hours), washing with cold hexane, drying) in 1500 ml of methylene chloride is then added dropwise thereto and the mixture is stirred for 15 hours at from −22° to −18° C. and finally for 1 hour at 0° C. The reaction mixture is taken up in 10 liters of ice-water and 12 liters of tert-butyl methyl ether and stirred vigorously for 7–10 minutes. The aqueous phase is separated off and extracted twice with 10 liters of ether; the organic phases are washed with 8 liters of water, 8 liters of saturated sodium hydrogen carbonate solution, 8 liters of water and 5 liters of brine, dried with sodium sulfate and concentrated by evaporation (→crystalline 5(S)-(Boc-amino)-4(S)-hydroxy-6-phenyl-hexanoic acid ethyl ester). The above intermediate is heated in 6500 ml of toluene and 230 ml of acetic acid under an argon atmosphere for 2.5 hours at 100° C. The cooled reaction mixture is poured onto 6 liters of ice-water, with stirring, and the aqueous phase is separated off and extracted twice with 2000 ml of toluene; the organic phases are washed with 5 liters of saturated sodium hydrogen carbonate solution, 5 liters of 40% sodium hydrogen sulfite solution, 4 liters of water and 4 liters of brine and dried with sodium sulfate. Concentration of the organic phases by evaporation to give a residue of about 300 g and the addition of 800 ml of hexane (stirred for several hours to complete the reaction) yield crystalline lactone which, according to HPLC, comprises approximately 10% of the (5R)-epimer TLC R$_f$ (E)= 0.08; t$_{Ret}$(II)=18.8 min). That material is used in the next step. The pure title compound can be obtained by column chromatography (SiO$_2$, hexane/ethyl acetate 2:1) TLC R$_f$ (E)=0.14; t$_{Ret}$(II)=19.2.

β) 5(S)-[1(S)-(Boc-amino)-2-phenylethyl]-3(R)-phenylmethyl-dihydrofuran-2-(3H)-one (A. K. Ghosh, S. P. McKee, and W. J. Thompson, J. Org. Chem. 56, 6500 (1991)). Under a nitrogen atmosphere, a solution of 1943 g (6.32 mol) of 5(S)-[(1S)-(Boc-amino)-2-phenylethyl]-dihydrofuran-2-(3H)-one in 12.0 liters of THF and 1.9 liters of 1,3-dimethyl-3,4,5,6-tetrahydro-2(1H)-pyrimidinone is cooled to −75° C. and, at an internal temperature of below −70° C., 14 000 ml of lithium bis (trimethylsilyl)amide (1M) in THF (Aldrich) are added and the mixture is then stirred for 20 minutes at −75° C. 835 ml (7.00 mol) of benzyl bromide are then added dropwise over a period of 1 hour, the internal temperature not being allowed to rise above −70° C., and the mixture is stirred for 30 minutes at −75° C. to complete the reaction. There are then added to the clear solution, at −75° to −70° C., 2320 ml of propionic acid (90 min) and then 2320 ml of water (1 hour), the temperature being allowed to rise to −10° C. The reaction mixture is poured onto 30 liters of ethyl acetate and 35 liters of 10% citric acid solution; the aqueous phase is separated off and extracted with 2×10 liters of ethyl acetate. The organic phases are washed with 3×12 liters of saturated sodium hydrogen carbonate solution, 20 liters of brine and 2×20 liters of water and concentrated, and the oily residue is taken up in 10 liters of toluene and concentrated by evaporation to a residual volume of about 5 liters. Filtration of the evaporation residue through 4 kg of Merck silica gel (0.063–0.200 mm), washing with toluene and crystallisation of the crude product from hexane (4 liters of hexane/kg of crude product) yield the title compound: TLC $R_f(D)$=0.54; FAB-MS $(M+H)^+$=414.]

1 h) 5(S)-(Boc-amino)-4(S)-hydroxy-6-phenyl-2(R)-phenylmethylhexanoic acid 176 ml of a 1M lithium hydroxide solution are added dropwise at 20° C. in the course of 10 minutes to a solution of 17.6 g of 5(S)-[1(S)-(Boc-amino)-2-phenylethyl]-3(R)-phenylmethyl-dihydrofuran-2-(3H)-one in 710 ml of ethylene glycol dimethyl ether and 352 ml of water. The reaction mixture is then stirred for 1.5 hours at room temperature and the solvent is evaporated. The residue is poured onto 1 liter of cold 10% citric acid and the acidic solution is extracted three times using 800 ml of ethyl acetate each time. The combined extracts are washed first with 800 ml of water and then with 800 ml of brine. After drying the organic solution over sodium sulfate, the solvent is distilled off. The crude title compound is used in the next stage without further purification. FAB-MS $(M+H)^+$=414.

1 i) 5(S)-(Boc-amino)-4(S)-(tert-butyldimethylsilyloxy)-6-phenyl-2(R)-phenylmethylhexanoic acid 8 g of imidazole and 10 g of tert-butyldimethylchlorosilane are added, with stirring, to a solution of 6.35 g of 5(S)-(Boc-amino)-4(S)-hydroxy-6-phenyl-2(R)-phenylmethylhexanoic acid in 90 ml of DMF. After being stirred for 18 hours at room temperature, the clear yellow solution is poured onto ice-water and extracted three times using 250 ml of ethyl acetate each time. The combined extracts are washed in succession three times with 10% citric acid, once with water, three times with aqueous saturated sodium hydrogen carbonate solution, once with water and finally with brine. After drying over sodium sulfate, the solvent is evaporated and the resulting tert-butyldimethylsilyl ether (13.5 g) is dissolved in 53 ml of THF and treated with 53 ml of acetic acid and 20 ml of water. After being stirred for 3 hours at room temperature, the mixture is poured onto water and extracted three times with ether. The combined ether extracts are washed twice with water and once with brine and dried over sodium sulfate. After concentration, the crude product is purified by column chromatography ($SiO_2$, hexane/ethyl acetate: 3.5/1.5) and the title compound obtained. TLC $R_f$ (D)=0.37; FAB-MS $(M+H)^+$=528.

1 j) 5(S)-(Boc-amino)-4(S)-(tert-butyldimethylsilyloxy)-6-phenyl-2(R)-phenylmethylhexanoyl-(L)-Val-(L)-Phe-morpholin-4-ylamide A solution of 250 mg of 5(S)-(Boc-amino)-4(S)-tert-butyldimethylsilyloxy)-6-phenyl-(R)-phenylmethyl-hexanoic acid in 3 ml of DMF with 230.5 mg of BOP, 70.4 mg of HOBT and 182.6 ml of N-methylmorpholine is stirred for 30 minutes at room temperature in approximately 2 ml of DMF, and then 189.5 mg of H-(L)-Val-(L)-Phe-morpholin-4-ylamide [preparation, see under 1 k) to 1 n)] are added. After 16 hours at room temperature, the reaction mixture is concentrated by evaporation and the residue is partitioned between three portions of ethyl acetate, water, saturated sodium hydrogen carbonate solution, water and brine, and the organic phases are dried with sodium sulfate and concentrated by evaporation, yielding the title compound as a crude product; TLC $R_f$ (A)=0.24; FAB-MS $(M+H)^+$=843.

1 k) Z-(L)-Phe-morpholin-4-ylamide

A solution of 4.49 g of Z-(L)-Phe-OH in 190 ml of methylene chloride is cooled to 0° C., and 3.09 g of DCC are added. After 20 minutes' stirring at 0° C., a solution of 1.31 ml of morpholine in 10 ml of methylene chloride is added dropwise over a period of 15 minutes. The reaction mixture is stirred for a further 24 hours at room temperature and, after the precipitated dicyclohexylurea has been filtered off, washed in succession with methylene chloride, aqueous sodium hydrogen carbonate solution and brine. Drying over sodium sulfate and concentration yield the crude title compound which is crystallised out from ether. TLC $R_f(B)$=0.55.

1 l) H-(L)-Phe-morpholin-4-ylamide

A solution of 5.5 g of Z-(L)-Phe-morpholin-4-ylamide with 1.5 g of 10% Pd/C in 150 ml of methanol is converted into the title compound by hydrogenolysis at room temperature for 1 hour with the calculated amount of hydrogen. After the catalyst is filtered off, the reaction mixture is concentrated and, after dilution with ethyl acetate, the resulting solution is washed with a saturated sodium hydrogen carbonate solution, dried over sodium sulfate and concentrated under reduced pressure. After column chromatography (analogously to Example 1 n)) the title compound is obtained in pure form. TLC $R_f(F)$=0.3.

1 m) Z-(L)-Val-(L)-Phe-morpholin-4-ylamide 1.75 g of DCC are added to a solution of 2.14 g of Z-(L)-Val-OH in 80 ml of absolute ice-cooled methylene chloride and after 20 minutes' stirring at that temperature 2 g of H-(L)-Phe-morpholin-4-ylamide are added dropwise over a period of 15 minutes. The reaction mixture is stirred for a further 24 hours at room temperature and the urea that has formed is filtered off. The filtrate is washed in succession with aqueous sodium hydrogen carbonate solution and brine and, after drying over sodium sulfate, concentrated. Stirring with ether, removal of the insoluble residue by filtration, and concentration yield the title compound which is processed further without additional purification. TLC $R_f(F)$=0.7.

1 n) H-(L)-Val-(L)-Phe-morpholin-4-ylamide

Analogously to Example 1l), 3.9 g of Z-(L)-Val-(L)-Phe-morpholin-4-ylamide are converted by hydrogenolysis using 0.5 g of 10% Pd/C in 150 ml of methanol into the crude title compound which is purified by column chromatography ($SiO_2$, methylene chloride to methylene chloride/methanol: 97.5 to 2.5 (v/v)). TLC $R_f(F)$=0.4.

EXAMPLE 2

Boc-Phe[C](p-$CH_3O$)Phe-(L)-Val-(L)-Phe-morpholin-4-ylamide

Analogously to Example 1), protection is removed from 417 mg (0.48 mmol) of 5(S)-(Boc-amino)-4(S)-(tert-butyldimethylsilyloxy)-6-phenyl-2(R)-(p-methoxyphenylmethyl)-hexanoyl-(L)-Val-(L)-Phe-morpholin-4-ylamide with 301 mg (0.95 mmol) of TBAF in 5 ml of DMF to give the title compound; TLC $R_f(F)$=0.4; $t_{Ret}(I)$=15.8 min; FAB-MS $(M+H)^+$=759.

The starting material is prepared as follows:
a) p-Methoxybenzyl iodide

A solution of 1.7 ml (12.8 mmol) of 4-methoxybenzyl chloride (Fluka; Buchs/Switzerland) in 25 ml of acetone is stirred with 9.4 g (62.6 mmol) of sodium iodide at room temperature. Gas chromatography of the reaction mixture after 90 minutes indicates that the reaction is complete, and the reaction mixture is therefore poured onto ether and washed with 10% sodium thiosulfate solution and brine. Drying of the organic phase with $Na_2SO_4$ and concentration by evaporation yield the title compound; $^1$H-NMR (200 MHz, $CD_3OD$: 3.78 (s, 3 H), 4.54 (s, 2 H), 6.8–6.95 and 7.2–7.4 (2m, each 2 H).

b) 5(S)-[1(S)-(Boc-amino)-2-phenyl-ethyl]-3(R)-(p-methoxy-phenylmethyl)-dihydrofuran-2-(3H)-one 2.98 g (9.74 mmol) of 5(S)-[1(S)-(Boc-amino)-2-phenylethyl]-dihydrofuran-2-(3H)-one dissolved in 40 ml of THF are deprotonated at $-75°$ C. with 19.5 ml of lithium bis(trimethylsilyl)amide 1M in THF and alkylated with 2.9 g (11.7 mmol) of p-methoxybenzyl iodide in 20 ml of THF (45 min). Column chromatography ($SiO_2$, hexane/ethyl acetate 2:1) and digestion using diisopropyl ether yield the pure title compound; TLC $R_f(D)=0.32$; $t_{Ret}(I)=16.7$ min.

c) 5(S)-(Boc-amino)-4(S)-hydroxy-6-phenyl-2(R)-(p-methoxyphenylmethyl)-hexanoic acid 1.7 g (3.99 mmol) of 5(S)-[1(S)-(Boc-amino)-2-phenylethyl]-3(R)-(p-methoxy-phenylmethyl)-dihydrofuran-2-(3H)-one in 43 ml of dimethoxyethane and 11 ml of water are hydrolysed with 16 ml of 1M lithium hydroxide solution. Stirring in ether yields the pure title compound: TLC $R_f(F)=0.53$; $t_{Ret}(I)=14.2$ min; FAB-MS $(M+Na)^+=466$.

d) 5(S)-(Boc-amino)-4(S)-(tert-butyldimethylsilyloxy)-6-phenyl-2(R)-(p-methoxyphenylmethyl)-hexanoic acid Analogously to Example 1i), 0.93 g (2.10 mmol) of 5(S)-(Boc-amino)-4(S)-hydroxy-6-phenyl-2(R)-(p-methoxy-phenylmethyl)-hexanoic acid in 20 ml of DMF is silylated with 1.4 g (9.64 mmol) of tert-butyldimethylchlorosilane and 1.17 g (17.2 mmol) of imidazole. The silyl ester function is hydrolysed with 1.7 g of potassium carbonate in methanol (23 ml)/THF (7 ml)/water (7 ml) and the crude product is stirred in hexane to give the title compound; $t_{Ret}(I)=20.6$ min; FAB-MS $(M+H)^+=558$.

e) 5(S)-(Boc-amino)-4(S)-(tert-butyldimethylsilyloxy)-6-phenyl-2(R)-(p-methoxyphenylmethyl)-hexanoyl-(L)-Val-(L)-Phe-morpholin-4-ylamide 300 mg (0.537 mmol) of 5(S)-(Boc-amino)-4(S)-(tert-butyldimethylsilyloxy)-6-phenyl-2(R)-(p-methoxyphenylmethyl)-hexanoic acid and 197 mg (0.59 mmol) of H-(L)-Val-(L)-Phe-morpholin-4-ylamide (Example 1 n)) in 5.2 ml of $NMM/CH_3CN$ 0.25M are reacted with 224 mg (0.59 mmol) of HBTU; $t_{Ret}(I)=22.1$ min; FAB-MS $(M+H)^+=873$.

f) 5(S)-[1(S)-(Boc-amino)-2-phenylethyl]-dihydrofuran-2-(3H)-one (Analogously to A. E. DeCamp et al., Tetrahedron Lett. 32, 1867 (1991).) Under a nitrogen atmosphere, 8.03 g of Zn/Cu (preparation: see R. D. Smith, H. E. Simmons, W. E. Parham, M. D. Bhasvar, Org. Synth., Coll. Vol 5, 855 (1973)) and 12.96 ml of dimethylacetamide are added to a solution of 17.4 g of 2-iodopropionic acid ethyl ester in 130 ml of toluene and the mixture is then stirred vigorously for 1 hour at room temperature and for 4 hours at 80° C. (yielding the corresponding zinc homoenolate solution). In a second apparatus (nitrogen atmosphere), 5.90 ml (53.8 mmol) of titanium tetrachloride are added to a solution of 5.58 ml (18.9 mmol) of tetraisopropyl orthotitanate in 1.64 ml of toluene and 91.8 ml of methylene chloride with slight cooling and the mixture is stirred for 15 minutes at room temperature (yielding a yellow solution) and cooled to $-40°$ C. (partial crystallisation of the trichlorotitanium isopropanolate occurs). The zinc homoenolate solution, which has cooled to room temperature, is decanted off from the metallic solid using a cannula and added dropwise to the trichlorotitanium isopropanolate, the temperature being maintained at $-40°$ C. to $-30°$ C. (yielding a deep-red solution), and the solution is heated to $-25°$ C. for 5 minutes and cooled again to $-40°$ C. A solution of 9.0 g of N-Boc-phenylalaninal (preparation: D. J. Kempf, J. Org. Chem. 51, 3921 (1986)) in 32.8 ml of methylene chloride is then added dropwise and the reaction mixture is stirred for 15 hours at about $-20°$ C. and finally at 0° C. The reaction mixture is poured onto 0.5 kg of ice-water and 0.5 liter of diethyl ether and stirred vigorously for 10 minutes. The aqueous phase is separated off and extracted with two portions of diethyl ether; the organic phases are washed with two portions of water, saturated sodium hydrogen carbonate solution and brine, dried with sodium sulfate and concentrated by evaporation, yielding as intermediate crystalline 5(S)-(Boc-amino)-4(S)-hydroxy-6-phenyl-hexanoic acid ethyl ester. That intermediate is heated in 195 ml of toluene and 9 ml of acetic acid at 80° C. for 2.5 hours. 0.5 ml of water is added to the reaction mixture and the organic phase is separated off and extracted with two portions of diethyl ether; the organic phases are washed with saturated sodium hydrogen carbonate solution, water and brine and dried with sodium sulfate. Partial concentration by evaporation of the organic phases and the addition of hexane yields the crystalline title compound which, according to analysis, comprises approximately 10% of the 4(R)-epimer (TLC $R_f(E)=0.08$). Column chromatography ($SiO_2$, hexane/ethyl acetate) yields the pure title compound; TLC $(R_f(E)=0.14$; $[\alpha]^D=17.7$ (c=1; ethanol).

EXAMPLE 3

5(S)-(Boc-amino)-4(S)-hydroxy-6-cyclohexyl-2(R)-(4-methoxyphenylmethyl)-hexanoyl-(L)-Val-(L)-Phe-morpholin-4-ylamide Analogously to Example 1, 3.93 g (4.469 mmol) of 5(S)-(Boc-amino)-4(S)-(tert-butyldimethylsilyloxy)-6-cyclohexyl-2(R)-(4-methoxyphenyl-methyl)-hexanoyl-(L)-Val-(L)-Phe-morpholin-4-ylamide in 15 ml of DMF are reacted with 2.82 g (8.94 mmol) of TBAF trihydrate to give the title compound. The title compound is purified by precipitation (hexane). TLC $R_f$ (B)=0.64; $t_{Ret}(III)=17.34$ min; FAB-MS $(M+H^+)=765$.

The starting compound is prepared as follows:

a) 5(S)-(Boc-amino)-4(S)-(tert-butyldimethyl)silyloxy-6-cyclohexyl-2(R)-(4-methoxyphenyl-methyl)-hexanoyl-(L)-Val-(L)-Phe-morpholin-4-ylamide A solution of 4 g (4.623 mmol) of 5(S)-(Boc-amino)-4 (S)-(tert-butyldimethyl)silyloxy-6-cyclohexyl-2(R)-(4-hydroxyphenyl-methyl)-hexanoyl-(L)-Val-(L)-Phe-morpholin-4-yl-amide in 70 ml of dioxane is treated with 6.02 g (18.49 mmol) of caesium carbonate and 9.1 ml (92.46 mmol) of methyl iodide and then heated to 50° C. After 1.25 hours the same amounts of caesium carbonate and methyl iodide are added again, and after 2.15 hours and 4 hours the same amount of methyl iodide is again added. After a total of 5.75 hours' stirring at 50° C., the reaction mixture is poured onto ice/water and extracted 3 times with methylene chloride. After drying over sodium sulfate, the reaction mixture is concentrated in a rotary evaporator. The title compound obtained after working-up is processed further without further purification. TLC $R_f$ (H)=0.36; $t_{Ret}(III)=24$ min; FAB-MS $(M+H^+)=880$.

b) 5(S)-(Boc-amino)-4(S)-(tert-butyldimethyl)silyloxy-6-cyclohexyl-2(R)-(4-hydroxyphenyl-methyl)-hexanoyl-(L)-Val-(L)-Phe-morpholin-4-ylamide 19.5 g (20.41 mmol) of 5(S)-(Boc-amino)-4(S)-(tert-butyldimethylsilyloxy)-6-cyclohexyl-2(R)-(4-benzyloxyphenyl-methyl)-hexanoyl-(L)-Val-(L)-Phe-morpholin-4-ylamide in 400 ml of methanol are hydrogenated in the presence of 4 g of 10% Pd/C. The title compound obtained after working-up is reacted further without additional purification; TLC $R_f$ (A) 0.28; $t_{Ret}$(III)= 21.99 min; FAB-MS (M+H$^+$)=866.

c) 5(S)-(Boc-amino)-4(S)-(tert-butyldimethyl)silyloxy-6-cyclohexyl-2(R)-(4-benzyloxyphenyl-methyl)-hexanoyl-(L)-Val-(L)-Phe-morpholin-4-ylamide 3 g (4.69 mmol) of 5(S)-(Boc-amino)-4(S)-(tert-butyldimethylsilyloxy)-6-cyclohexyl-2(R)-(4-benzyloxy-benzyl)-hexanoic acid in 40 ml of DMF with 1.91 g (5.16 mmol) of H-(L)-Val-(L)-Phe-morpholin-4-ylamide are cooled to 5° C. in an ice bath, and 0.783 ml (5.16 mmol) of DEPC and 2.3 ml (16.41 mmol) of triethylamine are added. After 1.5 hours' stirring at room temperature, the reaction mixture is poured onto water and extracted three times with ethyl acetate. The combined organic phases are washed with water, saturated sodium hydrogen carbonate solution (twice) and brine and, after drying over sodium sulfate, concentrated under reduced pressure. The title compound is purified by column chromatography (SiO$_2$, hexane/ethyl acetate: 1/1); TLC $R_f$(A)=0.3; $t_{Ret}$(III)=25.3 min; FAB-MS (M+H$^+$)=955.

d) 5(S)-(Boc-amino)-4(S)-(tert-butyldimethyl)siloxy-6-cyclohexyl-2(R)-(4-benzyloxy-benzyl)-hexanoic acid Analogously to Example 1 i), 28.8 g (54.8 mmol) of 5(S)-(Boc-amino)-4(S)-hydroxy-6-cyclohexyl-2(R)-(4-benzyloxy-benzyl-hexanoic acid in 288 ml of DMF are converted into the title compound with 35.8 g (237.6 mmol) of tert-butyldimethylchlorosilane and 30 g (237.6 mmol) of imidazole. The title compound is purified by column chromatography (SiO$_2$, hexane/ethyl acetate: 4/1 to 1/1); TLC $R_f$ (E)=0.33; $t_{Ret}$(III)=23.72 min.

e) 5(S)-(Boc-amino)-4(S)-hydroxy-6-cyclohexyl-2(R)-(4-benzyloxy-benzyl)-hexanoic acid Analogously to Example 1 h), 2.4 g (4.728 mmol) of 5(S)-[1(S)-(Boc-amino)-2-cyclohexylethyl]-3(R)-(4-benzyloxy-benzyl)-dihydrofuran-2-(3H)-one in 10 ml of 1,2-dimethoxyethane are reacted with 9.45 ml of 1M LiOH solution to give the title compound. The title compound is purified by crystallisation from hexane. TLC $R_f$ (E)=0.33; $t_{Ret}$(III)=18 min; FAB-MS (M+H$^+$)=526.

f) b) 5(S)-[1(S)-(Boc-amino)-2-cyclohexylethyl]-3(R)-(4-benzyloxybenzyl)-dihydrofuran-2-(3H)-one (Analogously to A. K. Ghosh et al., J. Org. Chem. 56, 6500 (1991)). 30.9 g (99.26 mmol) of 5(S)-[1(S)-(Boc-amino)-2-cyclohexylethyl]-dihydrofuran-2-(3H)-one with 200 ml (200 mmol) of lithium bis(trimethylsilyl)amide (Aldrich) 1M in THF at −75° C. is reacted to form the title compound by the dropwise addition of 34 g (104.8 mmol) of 4-benzyloxybenzyl iodide with 30 minutes' stirring at −75° C. to complete the reaction. After cooling again to −75° C., propionic acid and then water are added. The reaction mixture is heated to 0° C., diluted with ethyl acetate, washed with 10% citric acid solution, saturated sodium carbonate solution and brine, dried over sodium sulfate and concentrated by evaporation. The title compound is purified by column chromatography (SiO$_2$, hexane/ethyl acetate: 4/1 to 1/1) and crystallisation (hexane/ethyl acetate); TLC $R_f$ (C)= 0.33; $t_{Ret}$(III)=20.41 min; FAB-MS (M+H$^+$)=508.

g) 5(S)-[1(S)-(Boc-amino)-2-cyclohexylethyl]-dihydrofuran-2-(3H)-one

A solution of 5 g (16.37 mmol) of 5(S)-[1(S)-(Boc-amino)-2-phenylethyl]-dihydrofuran-2-(3H)-one in 50 ml of methanol is hydrogenated in the presence of 0.5 g of Nishimura catalyst under normal pressure for 2 hours at room temperature. Removal of the catalyst by filtration is followed by concentration in a rotary evaporator and drying under a high vacuum. TLC $R_f$ (D)=0.5; FAB-MS (M+H$^+$)= 312.

EXAMPLE 4

Inhibition of the Growth of a Human Mammary Carcinoma in the Mouse Model

2×6 female Balb/c nu/nu-mice (Bomholtgard, oestrogen-stimulated with 5 mg of oestradiol in a perforated plastics tube "Silastic®" (Dow Chemical, Michigan, USA)) are implanted with tumours by subcutaneous transplantation of fragments of human mammary carcinoma (about 25 mg) of the MCF-7 line (American Type Culture Collection, Maryland, USA; see H. D. Soule et al., J. Nat. Cancer Inst. 51, 1409–1416 (1973)). After the tumours have grown to a volume of about 30 to 100 mm$^3$ (after 13 days), 6 mice (test group) are each given twice daily over a period of 25 days a dose of 50 mg/kg of Boc-Phe[C]Phe-(L)-Val-(L)-Phe-morpholin-4-ylamide (dissolved in a concentration of 2 mg/ml in a 5% solution of dimethyl sulfoxide and 20% hydroxypropyl-β-cyclodextrin in water, prepared by dissolution of the test compound in dimethyl sulfoxide and dilution with aqueous hydroxypropyl-β-cyclodextrin solution). Administration is made orally by introducing the solution into the throat of experimental animals. The other 6 mice (control group) receive in parallel a placebo (5% solution of dimethyl sulfoxide in 20% aqueous hydroxypropyl-β-cyclodextrin solution). After 25 days (50 administrations) the following tumour volumes (mean value) are determined:

Control group (placebo):
  tumour volume 0.96 cm$^3$.
Test group (Boc-Phe[C]Phe-(L)-Val-(L)-Phe-morpholin-4-ylamide):
  tumour volume 0.30 cm$^3$.

There is a marked reduction in tumour growth in the animals treated with Boc-Phe[C]Phe-(L)-Val-(L)-Phe-morpholin-4-ylamide in comparison with the control group.

The tumour growth is determined by measuring the diameter along the longitudinal axis of the tumour (L) and perpendicular thereto (D) (in a living animal by means of a calliper gauge). The tumour volumes are calculated in accordance with the formula π×L×D$^2$/6 (Evans, B. D., et al., Brit. J. Cancer 45, 466–468 (1982)).

EXAMPLE 5

Gelatin Solution

A sterile-filtered aqueous solution of the compound of formula I mentioned in Example 1, which additionally comprises 20% cyclodextrin, and a sterile gelatin solution preserved with phenol are mixed together with heating under aseptic conditions in such a manner that 1.0 ml of solution having the following composition is obtained:

| active ingredient | 3 mg |
| --- | --- |
| gelatin | 150.0 mg |
| phenol | 4.7 mg |
| dist. water containing 20% cyclodextrins | 1.0 ml |

EXAMPLE 6

Sterile Dry Substance for Injection 5 mg of the compound of formula I mentioned in Example 1 are dissolved in 1 ml of an aqueous solution containing 20 mg of mannitol and 20% cyclodextrins as solubiliser. The solution is sterile-filtered and under aseptic conditions introduced into a 2 ml ampoule, deep-frozen and lyophilised. Before use, the lyophilisate is dissolved in 1 ml of distilled water or 1 ml of physiological saline solution. The solution is administered intramuscularly or intravenously. This formulation can also be introduced into double-chamber disposable syringes.

EXAMPLE 7

Nasal Spray 500 mg of finely ground powder (<5.0 μm) of the compound of formula I mentioned in Example 1 are suspended in a mixture of 3.5 ml of Myglyol 812® and 0.08 g of benzyl alcohol. That suspension is introduced into a container having a metering valve. 5.0 g of Freon 12® are introduced under pressure through the valve into the container. By shaking, the "Freon" is dissolved in the Myglyol/benzyl alcohol mixture. This spray container contains about 100 single doses which can be administered separately.

EXAMPLE 8

Film-Coated Tablets

For the preparation of 10 000 tablets each comprising 100 mg of active ingredient, the following constituents are processed:

| | |
|---|---|
| active ingredient | 1000 g |
| corn starch | 680 g |
| colloidal silicic acid | 200 g |
| magnesium stearate | 20 g |
| stearic acid | 50 g |
| sodium carboxymethyl starch | 250 g |
| water | quantum satis |

A mixture of the compound of formula I mentioned in Example 1, 50 g of corn starch and colloidal silicic acid is processed into a moist mass with a starch paste consisting of 250 g of corn starch and 2.2 kg of demineralised water. This mass is passed through a sieve of 3 mm mesh size and dried in a fluidised bed drier for 30 minutes at 45°. The dried granules are pressed through a sieve of 1 mm mesh size, mixed with a previously sieved mixture (1 mm sieve) of 330 g of corn starch, the magnesium stearate, the stearic acid and the sodium carboxymethyl starch and compressed to form slightly domed tablets.

EXAMPLE 9

Orally Administrable Dispersion 1

625 mg of the compound of formula I mentioned in Example 1, Boc-Phe[C]Phe-(L)-Val-(L)-Phe-morpholin-4-ylamide, and 625 mg of POPC (1-palmitoyl-2-oleoylphosphatidylcholine=1-hexadecanoyl-2-(9-cis-octadecenoyl)-3-sn-phosphatidylcholine) are dissolved in 25 ml of ethanol. The solution is diluted with ten times the amount of water. The ethanolic solution is for that purpose added dropwise at room temperature, at a rate of 10 ml/min, to the prescribed amount of water. The ethanol is removed from the mixture by tangential dialysis (Cross Flow Filtration) against 1750 ml of water (System: Minitan®, 700 cm² polyether sulphone membrane with an exclusion limit of 100 kD, supplied by Millipore (USA)). The mixture is concentrated to 15 mg of active ingredient by ultrafiltration using the same system. After the addition of 1.24 mg/ml of citric acid and 1.24 mg/ml of disodium hydrogen phosphate.2 H₂O to adjust the pH to 4.2 and the addition of 1 mg/ml of sorbic acid as antimicrobial preservative, the dispersion is concentrated to 15 mg/ml again and introduced into vials, for example having a capacity of 20 ml. The dispersion particles have a diameter of from 0.1–2 μm. They are stable for at least six months at from +2° to 8° C. and are suitable for oral administration.

EXAMPLE 10

Orally Administrable Dispersion 2

The preparation is carried out analogously to Example 9, except that 25 mg of active ingredient and 50 mg of POPC are used to prepare the ethanolic solution.

EXAMPLE 11

Orally Administrable Dispersion 3

The preparation is carried out analogously to Example 9, except that 25 mg of active ingredient and 125 mg of POPC are used to prepare the ethanolic solution.

EXAMPLE 12

Orally Administrable Dispersion 4

The preparation is carried out analogously to Example 9, except that 50 mg of active ingredient and 50 mg of POPC are used to prepare the ethanolic solution.

EXAMPLE 13

Orally Administrable Dispersion 5

The preparation is carried out analogously to any one of Examples 9 to 12, except that active ingredient and phosphatidylcholine from soybeans or phosphatidylcholine from egg yolk (70–100% pure) are used instead of POPC to prepare the ethanolic solution. If desired, an antioxidant, such as ascorbic acid, is added in a concentration of 5 mg/ml.

What is claimed is:

1. A method of treating a tumor of the pancreas, lungs, intestine, ovaries or breast in a warm-blooded animal in need thereof, comprising administering to said warm-blooded animal a tumour-treating effective amount of an inhibitor of HIV aspartate protease of formula I

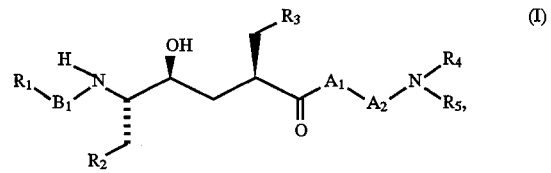

wherein $R_1$ is hydrogen; lower alkoxycarbonyl; heterocyclylcarbonyl; benzyloxycarbonyl which is unsubstituted or substituted by up to three radicals selected independently of one another from fluorine, halo-lower alkyl, lower alkanoyl, sulfo, lower alkylsulfonyl and cyano; heterocyclyloxycarbonyl wherein heterocyclyl is bonded via a carbon atom; one of the mentioned carbonyl radicals wherein the bonding carbonyl group has been replaced by a thiocarbonyl group; heterocyclylsulfonyl; lower alkylsulfonyl; or N-(heterocyclyl lower alkyl)-N-lower alkyl-aminocarbonyl;

$B_1$ is a bond or a bivalent residue of an a-amino acid bonded N-terminally to $R_1$ and C-terminally to the amino group at the carbon atom carrying $R_2$—$CH_2$—, $R_2$ and $R_3$ are each independently of the other phenyl or cyclohexyl, those radicals being unsubstituted or being substituted by from one to three radicals selected independently of one another from hydroxy, lower alkoxy, halogen, halo-lower alkyl, sulfo, lower alkylsulfonyl, cyano and nitro, $A_1$ is a bond between —C=O and $A_2$ or is a bivalent residue of an a-amino acid bonded N-terminally to the group —C=O and C-terminally to $A_2$, $A_2$ is a bivalent residue of an a-amino acid bonded N-terminally to $A_1$ and C-terminally to the group $NR_4R_5$, or $A_1$ and $A_2$ together form a bivalent residue of a dipeptide the central amide bond of which has been reduced and which is bonded N-terminally to the group —C=O and C-terminally to the group $NR_4R_5$, and $R_4$ and $R_5$ together with the bonding nitrogen atom form unsubstituted or substituted thiomorpholino or morpholino, or a salt of such a compound where salt-forming groups are present, or a hydroxy-protected derivative of such a compound or a salt thereof.

2. The method according to claim 1 in which the HIV aspartate protease inhibitor is a compound of formula I wherein $R_1$ is hydrogen, tert-butoxycarbonyl, isobutyloxycarbonyl, pyridine-3-carbonyl, morpholinocarbonyl, 3-benzofuranoyl, 1,2,3,4-tetrahydro-isoquinoline-3-carbonyl, benzyloxycarbonyl substituted by up to three radicals selected independently of one another from fluorine, halo-lower alkyl, lower alkanoyl, sulfo, lower alkylsulfonyl and cyano, or heterocyclyloxycarbonyl wherein heterocyclyl is bonded via a carbon atom and is selected from pyrrolyl, thienyl, imidazolyl, pyrazolyl, oxazolyl, thiazolyl, pyrazinyl, pyrimidinyl, indolyl, quinolyl, isoquinolyl, quinoxalinyl, β-carbolinyl and a fully or partially saturated derivative of those radicals, or wherein heterocyclyloxycarbonyl is absent as a definition of $R_1$, $B_1$ is a bond or a bivalent residue of an α-amino acid bonded N-terminally to $R_1$ and C-terminally to the amino group at the carbon atom carrying $R_2$—$CH_2$—, $R_2$ and $R_3$ are each independently of the other phenyl or cyclohexyl, those radicals being unsubstituted or substituted by one or two radicals selected independently of one another from hydroxy, methoxy, fluorine, sulfo, lower alkylsulfonyl, trifluoromethyl and cyano, $A_1$ is a bivalent residue of a hydrophobic α-amino acid bonded N-terminally to the group —C=O and C-terminally to $A_2$, $A_2$ is a bivalent residue of a hydrophobic α-amino acid bonded N-terminally to $A_1$ and C-terminally to the radical $NR_4R_5$, the said amino acid residues being in the (D)- or (L)-form, or $A_1$ and $A_2$ together form a bivalent residue of a dipeptide consisting of two hydrophobic α-amino acids the central amide bond of which has been reduced and which is bonded N-terminally to the group —C=O and C-terminally to the group $NR_4R_5$, and $R_4$ and $R_5$ together with the bonding nitrogen atom form thiomorpholino or morpholino;

the hydroxy group in compounds of formula I at the carbon atom adjacent to the carbon atom carrying the radical $R_2$—$CH_2$— being in free form or protected by lower alkanoyl, especially in free form; and in the definition of $R_1$ heterocyclyloxycarbonyl may also be omitted.

3. The method according to claim 1 in which the HIV aspartate protease inhibitor is a compound of formula I wherein $R_1$ is hydrogen, tert-butoxycarbonyl, isobutyloxycarbonyl, pyridine-3-carbonyl, morpholinocarbonyl, 3-benzofuranoyl, 1,2,3,4-tetrahydro-isoquinoline-3-carbonyl, morpholinosulfonyl or N-(2-pyridylmethyl)-N-methyl-aminocarbonyl, $B_1$ is a bond or a bivalent residue of the α-amino acid valine bonded N-terminally to $R_1$ and C-terminally to the amino group at the carbon atom carrying $R_2$—$CH_2$—, $R_2$ and $R_3$ are each independently of the other phenyl or cyclohexyl, those radicals being unsubstituted or substituted by one or two radicals selected independently of one another from hydroxy, methoxy, fluorine, trifluoromethyl and cyano, $A_1$ and $A_2$ together form a bivalent residue of a dipeptide of the formula Val-Phe, Ile-Phe, Val-Cha, Ile-Cha, Ile-Gly, Val-Val, Val-Gly, Val-(p-F-Phe), Val-Tyr, Val-(p-CH$_3$O-Phe), Gly-(p-F-Phe) or a derivative thereof having a reduced central amide bond of the formula Val(red)-Phe, bonded N-terminally to the group —C=O and C-terminally to the group $NR_4R_5$, and $R_4$ and $R_5$ together with the bonding nitrogen atom are thiomorpholino or morpholino, the hydroxy group in compounds of formula I at the carbon atom adjacent to the carbon atom carrying the radical $R_2$—$CH_2$— being free or being protected by acetyl.

4. The method according to claim 1 in which the HIV aspartate protease inhibitor is a compound of formula I wherein $R_1$ is lower alkoxycarbonyl, $B_1$ is a bond, $R_2$ and $R_3$ are phenyl, $A_1$ is valyl, $A_2$ is phenylalanyl, and $R_4$ and $R_5$ together with the bonding nitrogen atom are morpholino.

5. The method according to claim 1 in which the HIV aspartate protease inhibitor is a compound of formula I wherein $R_1$ is tert-butoxycarbonyl, $B_1$ is a bond, $R_2$ and $R_3$ are phenyl, $A_1$ is valyl, $A_2$ is phenylalanyl, and $R_4$ and $R_5$ together with the bonding nitrogen atom are morpholino.

6. The method according to claim 1, wherein the inhibitor of HIV aspartate protease is designated Boc-Phe[C]Phe-(L)-Val-(L)-Phe-morpholin-4-ylamide.

7. The method according to claim 1 in which the HIV aspartate protease inhibitor is a compound of formula I wherein $R_1$ is lower alkoxycarbonyl, $B_1$ is a bond, $R_2$ is phenyl and $R_3$ is 4-methoxyphenyl, $A_1$ is valyl, $A_2$ is phenylalanyl, and $R_4$ and $R_5$ together with the bonding nitrogen atom are morpholino.

8. The method according to claim 1 in which the HIV aspartate protease inhibitor is a compound of formula I wherein $R_1$ is lower alkoxycarbonyl, $B_1$ is a bond, $R_2$ is cyclohexyl and $R_3$ is 4-methoxyphenyl, $A_1$ is valyl, $A_2$ is phenylalanyl, and $R_4$ and $R_5$ together with the bonding nitrogen atom are morpholino.

9. The method of claim 1, wherein the compound of formula I is administered parenterally or enterally in a daily dose of approximately 3 mg to 10 g per 70 kg of body weight of said warm-blooded animal.

10. The method of claim 9, wherein the daily dose ranges from about 150 mg to about 1.5 g per 70 kg of body weight of said warm-blooded animal.

11. The method of claim 9, wherein said compound of formula I is administered intranasally, rectally, vaginally or orally.

* * * * *